(12) United States Patent
Ji et al.

(10) Patent No.: US 7,160,876 B2
(45) Date of Patent: Jan. 9, 2007

(54) FUSED BICYCLOHETEROCYCLE SUBSTITUTED QUINUCLIDINE DERIVATIVES

(75) Inventors: Jianguo Ji, Libertyville, IL (US); Tao Li, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 145 days.

(21) Appl. No.: 10/744,208

(22) Filed: Dec. 22, 2003

(65) Prior Publication Data

US 2005/0137184 A1 Jun. 23, 2005

(51) Int. Cl.
C07D 487/04 (2006.01)
C07D 471/04 (2006.01)
A61K 31/4375 (2006.01)
A61K 31/55 (2006.01)

(52) U.S. Cl. .......................... 514/213.01; 514/214.03; 514/305; 514/413; 514/256; 514/275; 514/255.05; 514/252.04; 548/453; 546/133; 546/137; 544/238; 544/333; 544/405

(58) Field of Classification Search ................ 540/585; 544/238, 333, 405; 546/133, 137; 548/453; 514/252.04, 255.05, 256, 275, 305, 413, 514/214.03, 213.01

See application file for complete search history.

(56) References Cited

U.S. PATENT DOCUMENTS 5,385,912 A  1/1995  Neuenschwander et al. ..... 514/305
2003/0199511 A1  10/2003  Li et al. ..................... 514/247

FOREIGN PATENT DOCUMENTS

| EP | 0458214 | 5/1991 |
|---|---|---|
| EP | 0456519 | 7/1994 |
| WO | WO92/15579 | 9/1992 |
| WO | WO94/18201 | 8/1994 |
| WO | WO95/03302 | 2/1995 |
| WO | WO95/31458 | 11/1995 |
| WO | WO96/12711 | 5/1996 |
| WO | WO97/17955 | 11/1996 |
| WO | WO97/17956 | 5/1997 |
| WO | WO97/17962 | 5/1997 |
| WO | WO97/20819 | 6/1997 |
| WO | WO99/10339 | 3/1999 |
| WO | WO00/71520 | 11/2000 |
| WO | WO03/062235 | 7/2003 |
| WO | 2004/016608 | 2/2004 |
| WO | 2004/022556 | 3/2004 |

OTHER PUBLICATIONS

Diaz GJ et al., *J. of Pharm and Toxicological Methods*, "The [3H]dofetilide binding assay is a predictive screening tool for hERG blockade and proarrhythmia: Comparison of intact cell and membrane preparations and effects of altering [K+]o", 50:187-199 (2004).

Holladay et al., "Neuronal Nicotinic Acetylcholine Receptors as Targets for Drug Discovery," *J. Med. Chem.*, 40(26): 4169-4194 (1997).

Brown et al., "Synthesis and Activity of a Novel Series of 3-Biarylquinuclidine Squalene Synthase Inhibitors," *J. Med. Chem.*, 39(15):2971-2979 (1996).

Adler et al, "Schizophrenia, sensory gating, and nicotinic receptors," Schizophrenia Bulletin 24(2):189-202 (1998).

Cordero-Erausquin et al., "Tonic nicotinic modulation of serotoninergic transmission in the spinal cord," PNAS 98(5):2803-2807 (2001).

Friedman et al., "A double blind placebo controlled trial of donepezil adjunctive treatment to risperidone for the cognitive impairment of schizophrenia," Biol. Psychiatry 51:349-357 (2002).

Heeschen et al., "Nicotine stimulates angiogenesis and promotes tumor growth and altherslerosis," Nature Medicine 7(7):833-839 (2001).

Heeshcen et al., "A novel angiogenic pathway mediated by non-neuronal nicotinic acetycholine receptors," Journal of Clinical Investigation 110(4):527-536 (2002).

Jonnala et al., "Relationship between the increased cell surface α7 nicotinic receptor expression and neuroprotection induced by several nicotinic receptor agonists," Journal of Neuroscience Research 66:565-572 (2001).

Kihara et al., "α7 Nicotinic receptor transduces signals to phosphatidylinositol 3-kinase to block A β-amyloid-induced neurotoxicity," Journal of Biological Chemistry 276(17):13541-13546 (2001).

Leonard et al., "Smoking and schizophrenia: abnormal nicotinic receptor expression," European Jouranal of Pharmacology 393:237-242 (2000).

(Continued)

Primary Examiner—Kahsay Habte
(74) Attorney, Agent, or Firm—Portia Chen

(57) ABSTRACT

Compounds of formula (I)

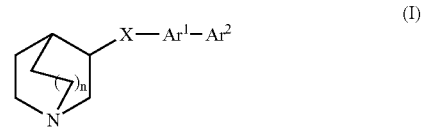

wherein n is 0, 1, or 2; X is O, S, —NH—, and —N-alkyl-; Ar¹ is a 6-membered aromatic ring; and Ar² is a fused bicycloheterocycle. The compounds are useful in treating conditions or disorders prevented by or ameliorated by α7 nAChR ligands. Also disclosed are pharmaceutical compositions having compounds of formula (I) and methods for using such compounds and compositions.

7 Claims, No Drawings

OTHER PUBLICATIONS

Levin, "Nicotinic receptor subtypes and cognitive function," J. Neurobiol. 53:633-640 (2002).

Liu et al., "β-Amyloid peptide blocks the response of α7-containing nicotinic receptors on hippocampal neurons," PNAS 98(8):4734-4739 (2001).

Rowley et al., "Current and novel approaches to the drug treatment of schizophrenia," Journal of Medicinal Chemistry 44(4):477-501 (2001).

Shimohama et al., "Nicotinic α7 receptors protect against glutamate neurotoxicity and neuronal ischemic damage," Brain Research 779:359-363 (1998).

Son et al., "Evidence suggesting that the mouse sperm acrosome reaction initiated by the zona pellucida involves an α7 nicotinic acetylcholine receptor," Biology of Reproduction 68:1348-1353 (2003).

Stevens et al., "Selective $α_7$-nicotinic agonists normalize inhibition of auditory response in DBA mice," Psychopharmacology 136:320-327 (1998).

Torii et al., "A versatile cycloaddition for the generation of pyrrolidine derivatives via C-N-C 1,3-dipoles," Chemistry Letters 747-748 (1996).

Wang et al., "Nicotinic acetylcholine receptor α7 subunit is an essential regulator of inflammation," Nature 421:384-388 (2003).

FUSED BICYCLOHETEROCYCLE SUBSTITUTED QUINUCLIDINE DERIVATIVES

TECHNICAL FIELD

The invention relates to fused bicycloheterocycle substituted quinuclidine derivatives, compositions comprising such compounds, and methods of treating conditions and disorders using such compounds and compositions.

DESCRIPTION OF RELATED TECHNOLOGY

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins, α2–α10 and β2–β4, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2 (\beta 2)_3$ (the α4β2 subtype), while another major population of receptors is comprised of the homomeric $(\alpha 7)_5$ (the α7 subtype).

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The α7 nAChRs have been shown to play a significant role in enhancing cognitive function, including aspects of learning, memory and attention (Levin, E. D., J. Neurobiol. 53: 633–640, 2002). For example, α7 nAChRs have been linked to conditions and disorders related to attention deficit disorder, attention deficit hyperactivity disorder (ADHD), Alzheimer's disease (AD), mild cognitive impairment, senile dementia, dementia associated with Lewy bodies, dementia associated with Down's syndrome, AIDS dementia, Pick's Disease, as well as cognitive deficits associated with schizophrenia, among other systemic activities.

The activity at the α7 nAChRs can be modified or regulated by the administration of α7 nAChR ligands. The ligands can exhibit antagonist, agonist, partial agonist, or inverse agonist properties. Thus, α7 ligands have potential in treatment of various cognitive disorders.

Although various classes of compounds demonstrating α7 nAChR-modulating activity exist, it would be beneficial to provide additional compounds demonstrating activity at the α7 nAChRs that can be incorporated into pharmaceutical compositions useful for therapeutic methods. Specifically, it would be beneficial to provide compounds that interact selectively with α7-containing neuronal nAChRs compared to other subtypes.

SUMMARY OF THE INVENTION

The invention is directed to fused bicycloheterocycle substituted quinuclidine compounds as well as compositions comprising such compounds, and method of using the same. Compounds of the invention have the formula:

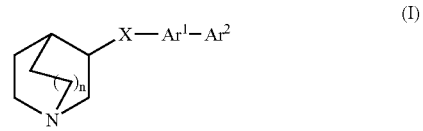

or a pharmaceutically acceptable salt, ester, amide, or prodrug thereof, wherein:

n is 0, 1, or 2;

X is selected from the group consisting of O, S, and $NR^1$;

$Ar^1$ is a 6-membered aromatic ring containing 0, 1, 2, 3, or 4 nitrogen atoms;

$Ar^2$ is a group of the formula:

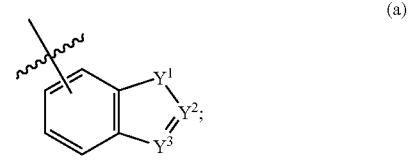

$Y^1$ is independently selected from O, S, $N(R^2)$, and $C(R^3)$;

$Y^2$ and $Y^3$ are each independently selected from the group consisting of N and $C(R^3)$;

$R^1$ and $R^2$ at each occurrence are each independently selected from the group consisting of hydrogen and alkyl;

$R^3$ at each occurrence is independently selected from the group consisting of hydrogen, halogen, alkyl, aryl, —$OR^4$, —$NR^5R^6$; and $R^4$ is selected from the group consisting of hydrogen, alkyl, aryl, alkylcarbonyl, and arylcarbonyl;

$R^5$ and $R^6$ at each occurrence are each independently selected from the group consisting of hydrogen, alkyl, aryl, alkylcarbonyl, alkoxycarbonyl, aryloxycarbonyl, and arylcarbonyl, provided that one of $R^5$ and $R^6$ is hydrogen or alkyl.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly α7 nAChR activity.

Yet another aspect of the invention relates to a method of selectively modulating to nAChR activity, for example α7 nAChR activity. The method is useful for treating and/or preventing conditions and disorders related to α7 nAChR activity modulation in mammals. More particularly, the method is useful for conditions and disorders related to attention deficit disorder, attention deficit hyperactivity disorder (ADHD), Alzheimer's disease (AD), mild cognitive impairment, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, need for new blood vessel growth associated with wound healing, need for new blood vessel growth associated with vascularization of skin grafts, and lack of circulation, more particularly circulation around a vascular occlusion, among other systemic activities.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl", as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy", as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl", as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy", as used herein, means an alkyl group as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy", as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl", as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl", as used herein, means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxyimino", as used herein, means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl", as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl", as used herein, means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl", as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio", as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl", as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido", as used herein, means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl", as used herein, means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —$NR_AR_B$, $(NR_AR_B)$alkyl, $(NR_AR_B)$alkoxy, $(NR_AR_B)$carbonyl, and $(NR_AR_B)$sulfonyl.

The term "aryloxycarbonyl", as used herein, means an aryl group, as defined herein, or a benzyl group appended to the parent molecular moiety through a carbonyl group, represented by —C(O)—, as defined herein. Representative examples of alkoxycarbonyl include, but are not limited to, phenoxycarbonyl and benzyloxycarbonyl.

The term "arylsulfonyl", as used herein, means an aryl group, as defined herein, appended to the parent molecular moiety through a sulfonyl group, as defined herein. Representative examples of arylsulfonyl include, but are not limited to, phenylsulfonyl, (methylaminophenyl)sulfonyl, (dimethylaminophenyl)sulfonyl, and (naphthyl)sulfonyl.

The term "carbonyl", as used herein, means a —C(O)— group.

The term "carboxy", as used herein, means a —CO$_2$H group.

The term "cyano", as used herein, means a —CN group.

The term "formyl", as used herein, means a —C(O)H group.

The term "halo" or "halogen", as used herein, means —Cl, —Br, —I or —F.

The term "haloalkoxy", as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl", as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl" means an aromatic five- or six-membered ring containing 1, 2, 3, or 4 heteroatoms independently selected from nitrogen, oxygen, or sulfur. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridinyl, pyrimidinyl, pyrrolyl, tetrazolyl, thiadiazolyl, thiazolyl, thienyl, triazinyl, and triazolyl.

The heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl.

The term "bicyclic heteroaryl" refers to fused aromatic nine- and ten-membered bicyclic rings containing 1, 2, 3, or 4 heteroatoms independently selected from nitrogen, oxygen, or sulfur, or a tautomer thereof. The bicyclic heteroaryl groups are connected to the parent molecular moiety through a carbon or nitrogen atom. Representative examples of bicyclic heteroaryl rings include, but are not limited to, indolyl, benzothiazolyl, benzofuranyl, isoquinolinyl, and quinolinyl. Bicyclic heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl.

The term "hydroxy", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto", as used herein, means a —SH group.

The term "nitro", as used herein, means a —NO$_2$ group.

The term "—NR$_A$R$_B$", as used herein, means two groups, R$_A$ and R$_B$, which are appended to the parent molecular moiety through a nitrogen atom. R$_A$ and R$_B$ are each independently hydrogen, alkyl, alkylcarbonyl, or formyl. Representative examples of —NR$_A$R$_B$ include, but are not limited to, amino, methylamino, acetylamino, and acetylmethylamino.

The term "(NR$_A$R$_B$)alkyl", as used herein, means a —NR$_A$R$_B$ group, as defined herein, appended to the parent molecular moiety through an alkyl group, as defined herein. Representative examples of (NR$_A$R$_B$)alkyl include, but are not limited to, (amino)methyl, (dimethylamino)methyl, and (ethylamino)methyl.

The term "(NR$_A$R$_B$)alkoxy", as used herein, means a —NR$_A$R$_B$ group, as defined herein, appended to the parent molecular moiety through an alkoxy group, as defined herein. Representative examples of (NR$_A$R$_B$)alkoxy include, but are not limited to, (amino)methoxy, (dimethylamino)methoxy, and (diethylamino)ethoxy.

The term "(NR$_A$R$_B$)carbonyl", as used herein, means a —NR$_A$R$_B$ group, as defined herein, appended to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, and (ethylmethylamino)carbonyl.

The term "(NR$_A$R$_B$)sulfonyl", as used herein, means a —NR$_A$R$_B$ group, as defined herein, appended to the parent molecular moiety through a sulfonyl group, as defined herein. Representative examples of (NR$_A$R$_B$)sulfonyl include, but are not limited to, aminosulfonyl, (methylamino)sulfonyl, (dimethylamino)sulfonyl, and (ethylmethylamino)sulfonyl.

The term "sulfonyl", as used herein, means a —S(O)$_2$— group.

The term "thioalkoxy", as used herein, means an alkyl group, as defined herein, appended to the parent molecular moiety through a sulfur atom. Representative examples of thioalkoxy include, but are no limited to, methylthio, ethylthio, and propylthio.

Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric (α7)$_5$ receptors and α7* receptors, which denote a nAChR containing at least one α7 subunit.

Compounds of the Invention

Compounds of the invention can have the formula (I) as described above. More particularly, compounds of formula (I) can include, but are not limited to, compounds wherein Ar$^1$ is a group of the formula:

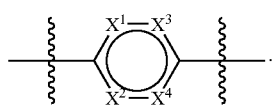

(b)

In a group of formula (b), X$^1$, X$^2$, X$^3$, and X$^4$ are each independently selected from the group consisting of N and —CR$^{10}$, wherein R$^{10}$ at each occurrence is independently selected from the group consisting of hydrogen and alkyl. Preferably, at least one of X$^1$, X$^2$, X$^3$, and X$^4$ is —CR$^{10}$, such that group of formula (b) contains 0, 1, 2, or 3 nitrogen atoms.

Specific examples of groups for Ar$^1$ are, for example,

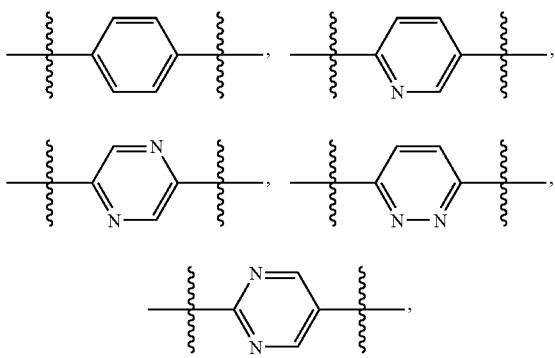

and the like.

Specific examples of groups for Ar$^2$ in a compound of formula (I) are, for example,

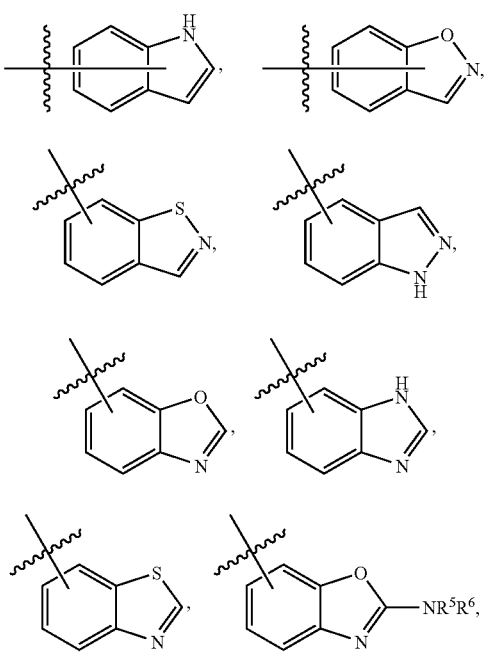

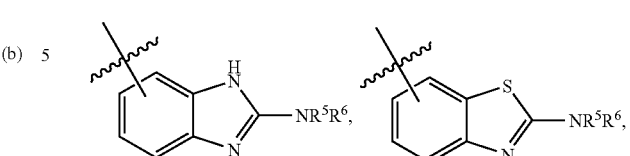

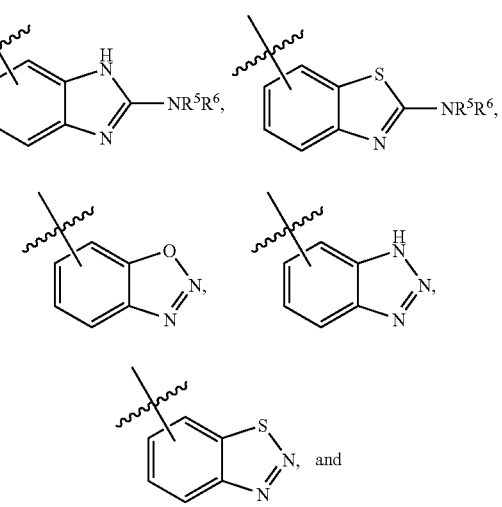

and the like.

Specific embodiments contemplated as part of the invention include, but are not limited to, compounds of formula (I), as defined, wherein:

3-[4-(1-azabicyclo[2.2.2]oct-3-yloxy)phenyl]-1H-indole;
4-[4-(1-azabicyclo[2.2.2]oct-3-yloxy)phenyl]-1H-indole;
5-[4-(1-azabicyclo[2.2.2]oct-3-yloxy)phenyl]-1H-indole;
5-{4-[(3R)-1-azabicyclo[2.2.2]oct-3-yloxy]phenyl}-1H-indole;
6-[4-(1-azabicyclo[2.2.2]oct-3-yloxy)phenyl]-1H-indole;
2-[4-(1-azabicyclo[2.2.2]oct-3-yloxy)phenyl]-1H-indole;
5-[6-(1-azabicyclo[2.2.2]oct-3-yloxy)pyridazin-3-yl]-1H-indole;
4-[6-(1-azabicyclo[2.2.2]oct-3-yloxy)pyridazin-3-yl]-1H-indole;
5-{6-[(3R)-1-azabicyclo[2.2.2]oct-3-yloxy]pyridazin-3-yl}-1H-indole;
5-{6-[(3R)-1-azabicyclo[2.2.2]oct-3-yloxy]pyridazin-3-yl}-3-methyl-1H-indole;
5-{2-[(3R)-1-azabicyclo[2.2.2]oct-3-yloxy]pyrimidin-5-yl}-1H-indole;
4-{2-[(3R)-1-azabicyclo[2.2.2]oct-3-yloxy]pyrimidin-5-yl}-1H-indole;
5-{2-[(3S)-1-azabicyclo[2.2.2]oct-3-yloxy]pyrimidin-5-yl}-1H-indole;
5-[4-(1-azabicyclo[2.2.2]oct-3-yloxy)phenyl]-3-methyl-1H-indazole;
6-[4-(1-azabicyclo[2.2.2]oct-3-yloxy)phenyl]-1,3-benzothiazol-2-amine;
N-[4-(3-methyl-1H-indazol-5-yl)phenyl]quinuclidin-3-amine;

or pharmaceutically acceptable salts, esters, amides, and prodrugs thereof.

Compound names are assigned by using AUTONOM naming software, which is provided by MDL Information Systems GmbH (formerly known as Beilstein Informationssysteme) of Frankfurt, Germany, and is part of the CHEMDRAW® ULTRA v. 6.0.2 software suite.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13–30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

As used in the descriptions of the schemes and the examples, certain abbreviations are intended to have the following meanings: Ac for acetyl; Bu for butyl; dba for dibenzylidene acetone; DEAD for diethyl azodicarboxylate; DMSO for dimethylsulfoxide; EtOAc for ethyl acetate; EtOH for ethanol; Et$_3$N for triethylamine; Et$_2$O for diethyl ether; HPLC for high pressure liquid chromatography; $^i$Pr for isopropyl; Me for methyl; MeOH for methanol; NBS for N-bromosuccinimide; OAc for acetoxy; o-tol. for o-toluene; Ph for phenyl; t-Bu for tert-butyl; TFA for trifluoroacetic acid; and THF for tetrahydrofuran.

The reactions exemplified in the schemes are performed in a solvent appropriate to the reagents and materials employed and suitable for the transformations being effected. The described transformations may require modifying the order of the synthetic steps or selecting one particular process scheme over another in order to obtain a desired compound of the invention, depending on the functionality present on the molecule.

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoracetyl. More particularly, the Boc protecting group may be removed by treatment with an acid such as trifluoroacetic acid or hydrochloric acid. The Cbz and Bn protecting groups may be removed by catalytic hydrogenation. The acetyl and trifluoracetyl protecting groups may be removed by a hydroxide ion.

The methods described below can entail use of various enantiomers. Where the stereochemistry is shown in the Schemes, it is intended for illustrative purposes only.

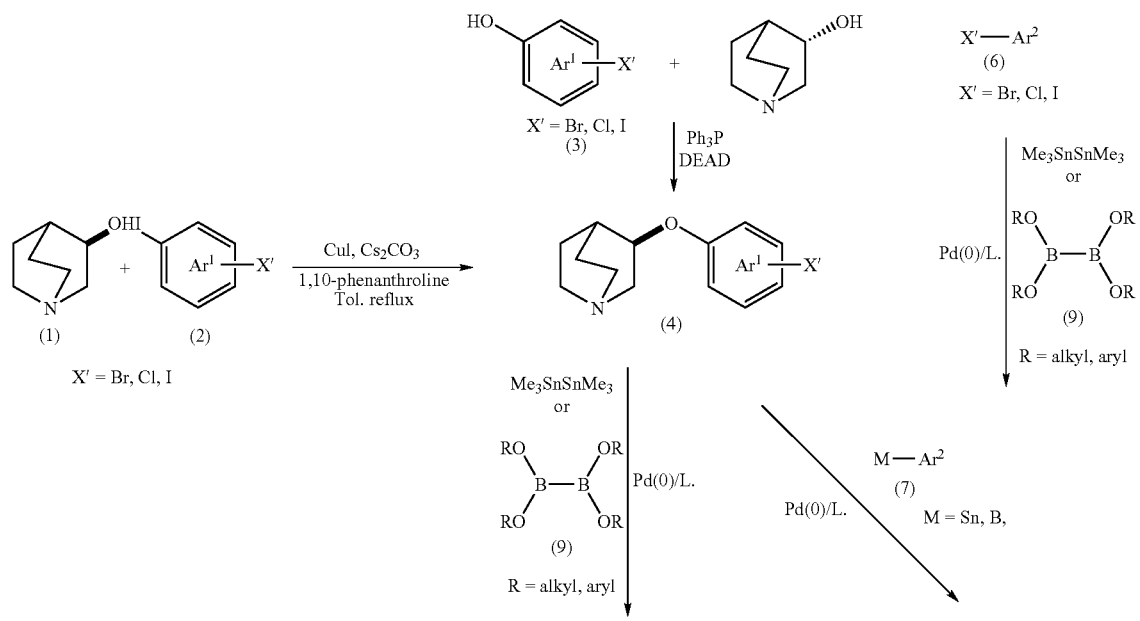

Scheme 1

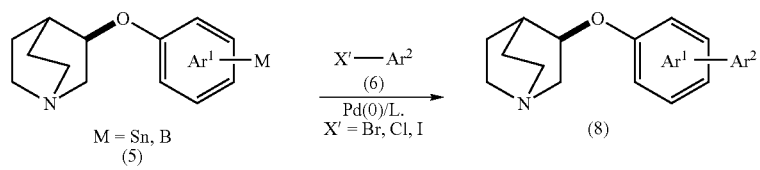

Quinuclidine ethers of general formula (8), wherein Ar[1] and Ar[2] are as defined in formula (I), can be prepared as described in Scheme 1. 3-Quinuclidinol of formula (1) is treated with a halophenyl iodide of formula (2), wherein X' is bromide, chloride, or iodide, with CuI and $Cs_2CO_3$ in 1,10-phenanthroline as described in Org. Lett., 2002, 4, 973, to obtain a halophenoxy quinuclidine of formula (4). Alternatively, a compound of formula can be obtained by treating 3-quinuclidinol with a halo phenyl alcohol of formula (3), wherein X' is bromide, chloride, or iodide, and diethyl azodicarboxylate in the presence of a phosphine, such as triphenylphosphine.

Compounds of formula (4) can be treated with hexamethylditin or diboron of formula (9), such as bis(pinacolato)diboron and bis(catecholato)diboron, wherein R is hydrogen, alkyl, butyloxycarbonyl, or benzyloxycarbonyl, in the presence of a palladium catalyst to provide the corresponding tin or boronic acid of formula (5), which is reacted with a desired halide of a fused bicycloheterocycle represented by Ar[2] of formula (6), wherein X' is bromide, chloride, or iodide, to provide compounds of formula (8). Alternatively, halides of a desired Ar[2] group can be treated with hexamethylditin or diboron of formula (9), such as bis(pinacolato)diboron and bis(catecholato)diboron, in the presence of a palladium catalyst to provide a corresponding tin or boronic acid reagent that is reacted with a compound of formula (4) in the presence of a palladium catalyst to provide a compound of formula (8).

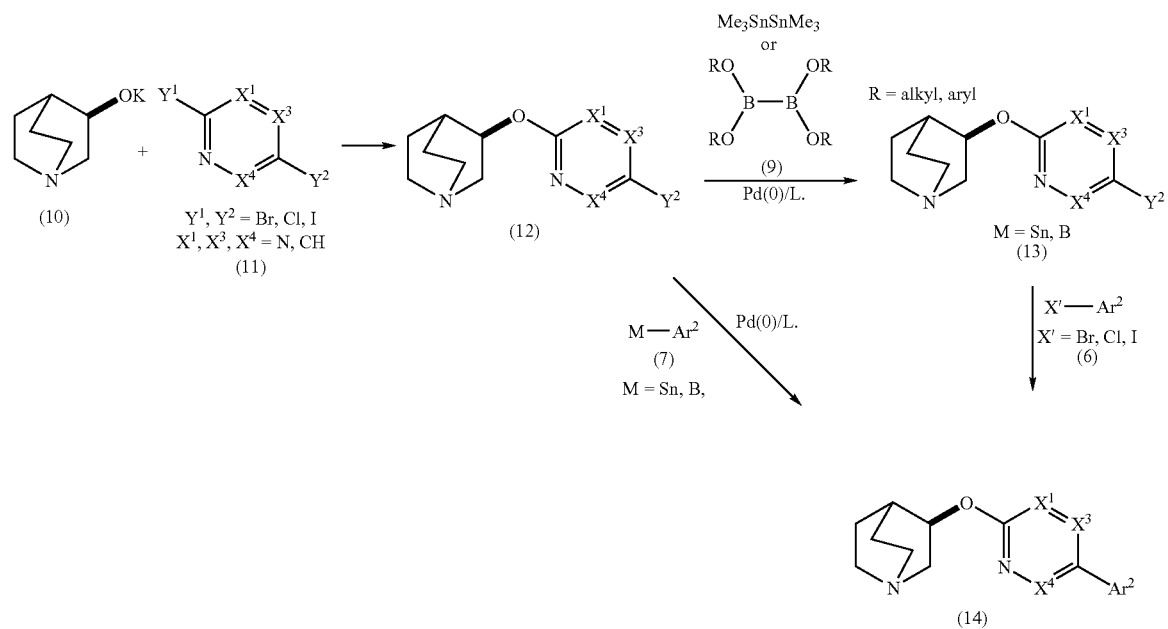

Quinuclidine ethers of formula (14), wherein $Ar^1$ is a nitrogen-containing heteroaryl, for example pyridazine, and $Ar^2$ is as defined for formula (I), can be prepared as shown in Scheme 2. Potassium quinuclidinoxide (10) can be reacted with a dihaloaromatic ring, for example, dichloropyridazine, of formula (11) to obtain a quinuclidine ether of formula (12). The quinuclidine ether can be reacted with a suitable tin or boron reagent, as described in Scheme 1, to provide a fused bicycloheterocycle substituted quinuclidine ether of formula (14). Alternatively, the quinuclidine ether of formula (12) can be treated with hexamethylditin or diboron of formula (9), such as bis(pinacolato)diboron and bis(catecholato)diboron, to activate the aromatic group to provide (13), wherein M is tin or boronic acid ester, and further treated with a halide of a desired group $Ar^2$ in the presence of a palladium catalyst to provide compounds of formula (14).

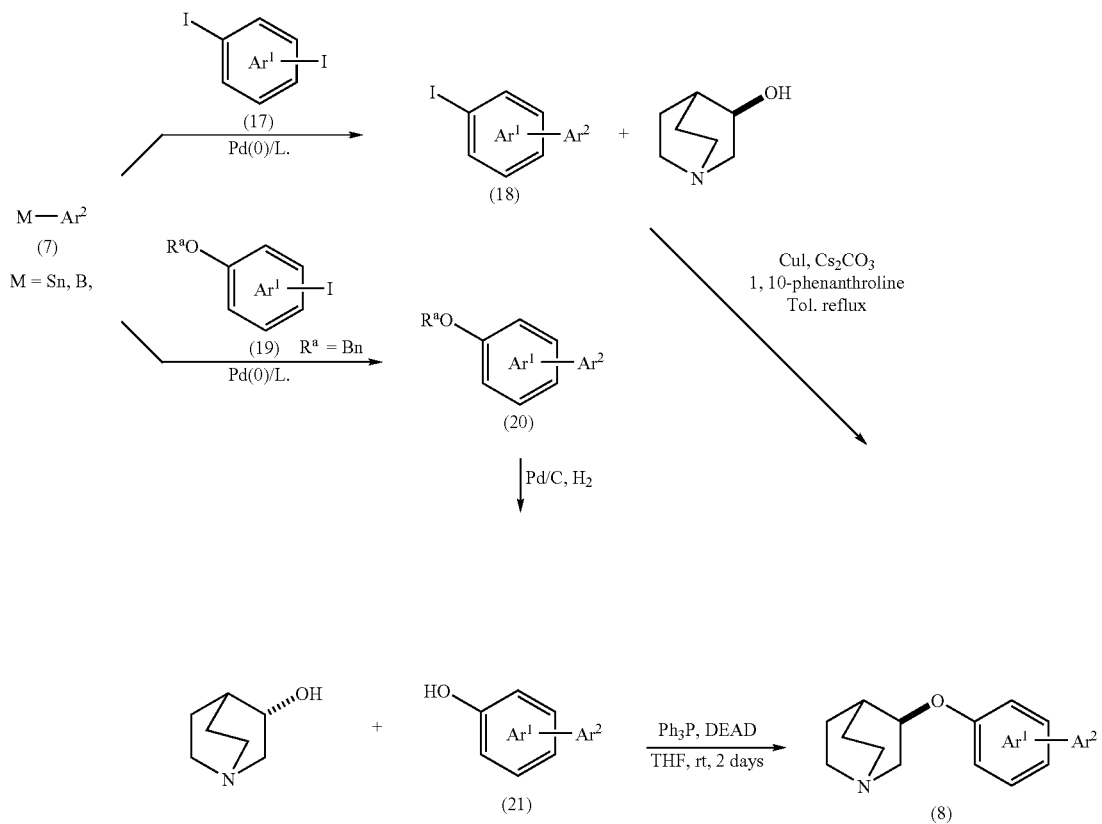

Scheme 3

Quinuclidine ethers of formula (8), wherein $Ar^1$ and $Ar^2$ are as defined for formula (I) also can be obtained by the methods described in Scheme 3. The activated tin or boronic acid reagent of formula (7) can be coupled with the diiodoaromatic ring of formula (17) in the presence of a palladium catalyst to provide a compound of formula (18). Compounds of formula (18) can be reacted with 3-quinuclidinol and CuI with $Cs_2CO_3$ in 1,10-phenanthroline as described in Org. Lett. 2002, 4, 973, to provide a desired compound of formula (8).

Alternatively, the compound of formula (7) is treated with a compound of formula (19), wherein $R^a$ is benzyl, in the presence of a palladium catalyst to provide a compound of formula (20). Compounds of formula (20), wherein $R^a$ is benzyl, are hydrogenated to provide compounds of formula (21) under standard hydrogenation conditions, for example Pd/C, and further treated with 3-quinuclidinol in the presence of a phosphine, for example triphenylphosphine, and diethyl azodicarboxylate to provide compounds of formula (8).

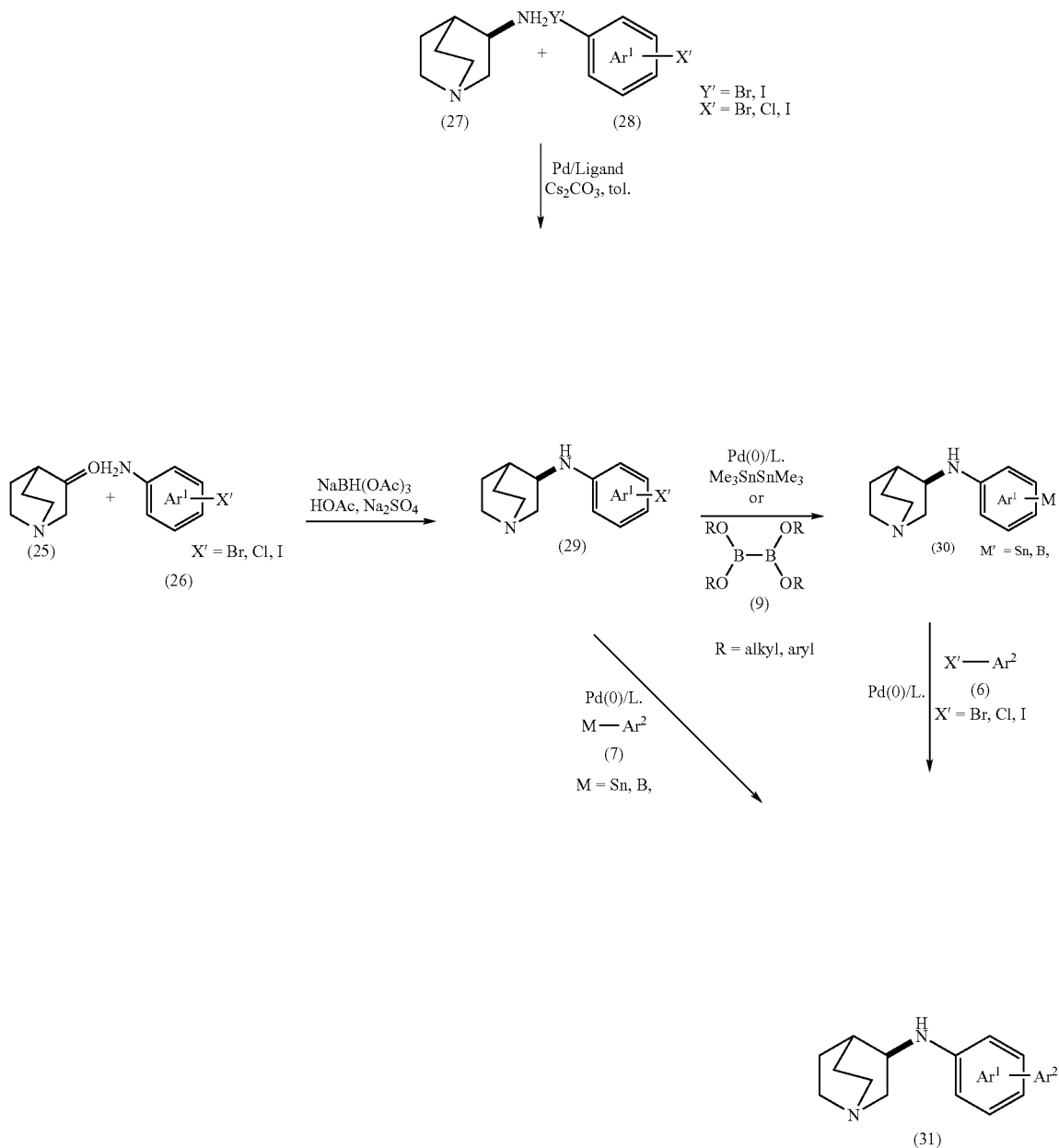

Compounds of formula (31), wherein X is —NH— and Ar¹ and Ar² are as described for compounds of formula (I), can be prepared as shown in Scheme 4. 3-Quinuclidinone (25) and a haloarylamine of formula (26), wherein X' is bromide, chloride, or iodide, can be treated with sodium triacetoxy borohydride and acetic acid in Na₂SO₄ to provide a compound of formula (29). Alternatively, a compound of formula (29) can be obtained by treating 3-aminoquinuclidine (27) with haloaromatic group as described in formula (28) with Cs₂CO₃ in the presence of palladium catalyst, preferably in toluene. A compound of formula (29) can be treated with a tin or diboron of formula (9), such as bis(pinacolato)diboron and bis(catecholato)diboron, under conditions previously described to provide the corresponding tin or boronic acid reagent of formula (30), which can be reacted with the halide of a desired group represented by Ar² in a compound of formula (I) to provide a compound of formula (31). Alternatively, the compound of formula (29) is treated with a tin or boronic acid ester of the desired Ar² group in the presence of a palladium catalyst to provide a compound of formula (31).

Scheme 5

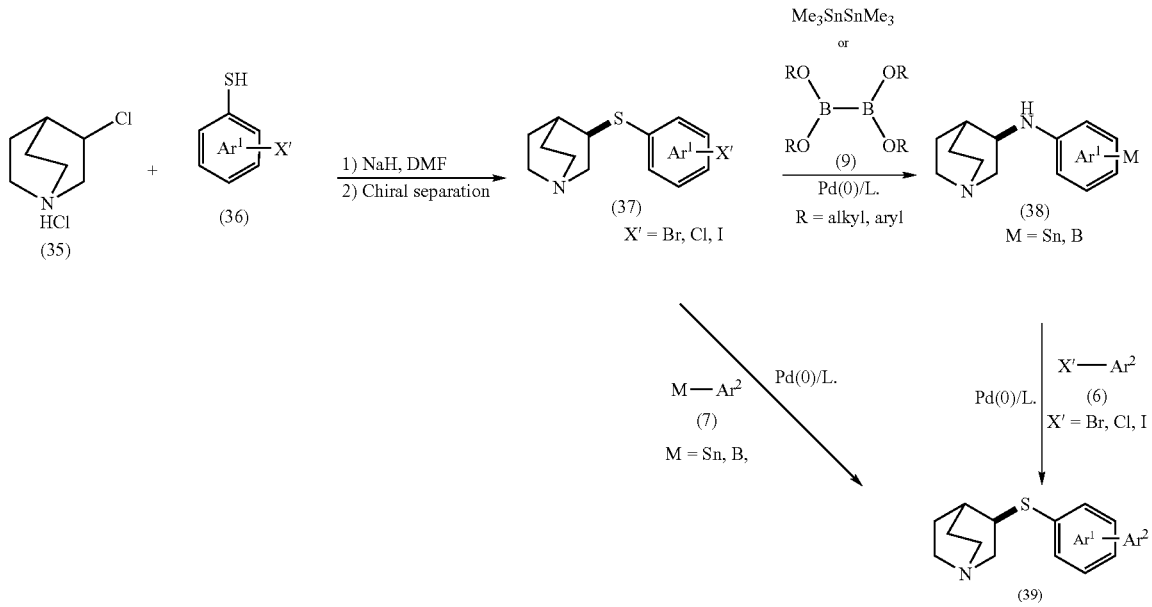

Compounds of formula (39), wherein X is S and Ar¹ and Ar² are as defined in a compound of formula (I), can be prepared as shown in Scheme 5. 3-Chloroquinuclidine (35) can be reacted with a haloarylthiol of formula (36), wherein X' is bromide, chloride, or iodide, to provide a compound of formula (37). The compound of formula (37) can be treated with a tin or boron reagent of a desired group for Ar² as described for a compound of formula (I) to provide a compound of formula (39). Alternatively, the compound of formula (37) can be reacted with a hexamethylditin or diboron reagent of formula (9), such as bis(pinacolato) diboron and bis(catecholato)diboron, in the presence of a palladium catalyst to provide a compound of formula (38), which is reacted with the halide of a desired Ar² group in the presence of a palladium catalyst to provide a compound of formula (39).

Scheme 6

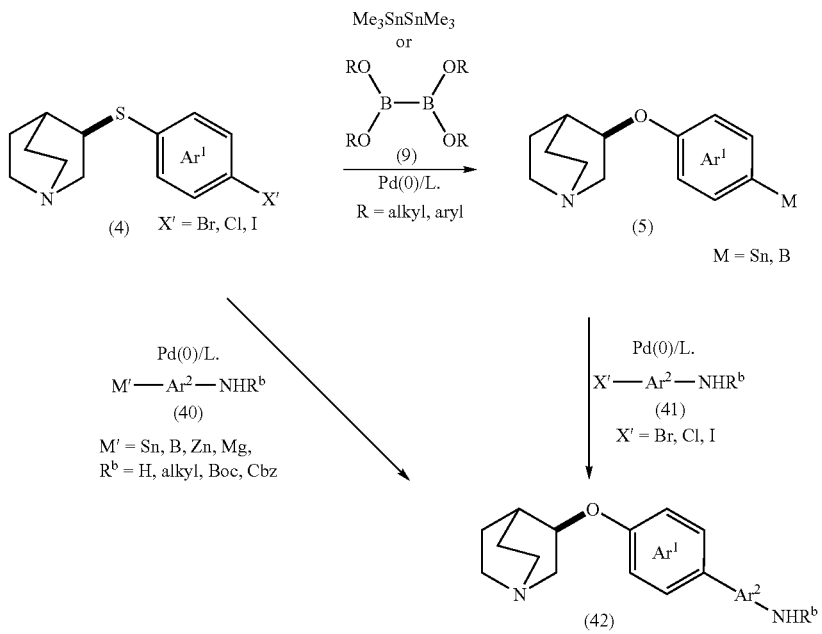

Compounds of formula (42), wherein X is O, $R^3$ is $NHR^b$, and $Ar^1$, $Ar^2$ are defined as in compounds of formula (I), can be prepared as shown in Scheme 6. Compounds of formula (4) obtained as shown in Scheme 1 can be treated with a metal of the desired amino-substituted $Ar^2$ group, as described for compounds of formula (I) to provide compounds of formula (42), wherein $R^b$ is hydrogen, alkyl, butyloxycarbonyl, or benzyloxycarbonyl. Compounds of formula (4) can be treated with a hexamethylditin or diboron reagent of formula (9), such as bis(pinacolato)diboron and bis(catecholato)diboron, in the presence of a palladium catalyst to provide the corresponding tin or boronic acid of formula (5), which is reacted with a desired halide of an amine-substituted fused bicycloheterocycle represented by $Ar^2$ of formula (41), wherein X' is bromide, chloride, or iodide, to provide compounds of formula (42).

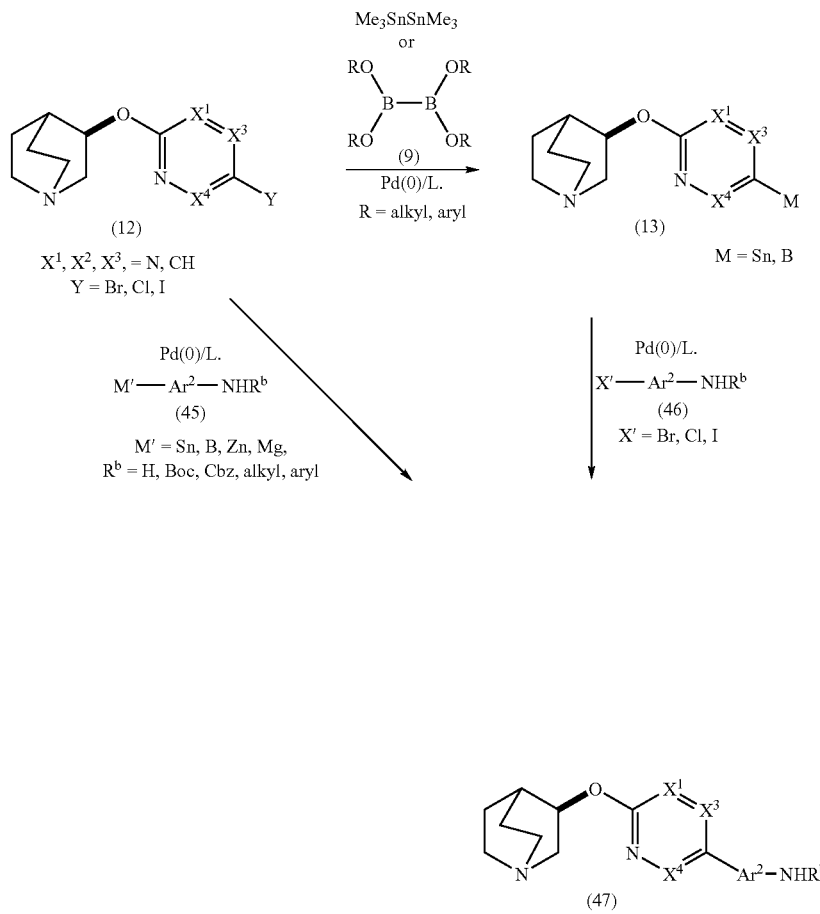

Compounds of formula (47), wherein X is O, $Ar^1$ is a nitrogen containing aromatic group, for example pyridazine, $R^3$ is $NHR^b$, as previously defined, and $Ar^2$ is defined as in compounds of formula (I), can be prepared as shown in Scheme 7. Compounds of formula (12), which can be obtained as shown in Scheme 2, are treated with a metal of the desired amino-substituted $Ar^2$ group, as described for compounds of formula (I), of formula (45) to provide compounds of formula (47). Compounds of formula (12) also can be treated with a hexamethylditin or diboron reagent of formula (9), such as bis(pinacolato)diboron and bis(catecholato)diboron, in the presence of a palladium catalyst to provide the corresponding tin or boronic acid of formula (13), which is reacted with a desired halide of an amine-substituted fused bicycloheterocycle represented by $Ar^2$ of formula (46), wherein X' is bromide, chloride, or iodide, to provide compounds of formula (47).

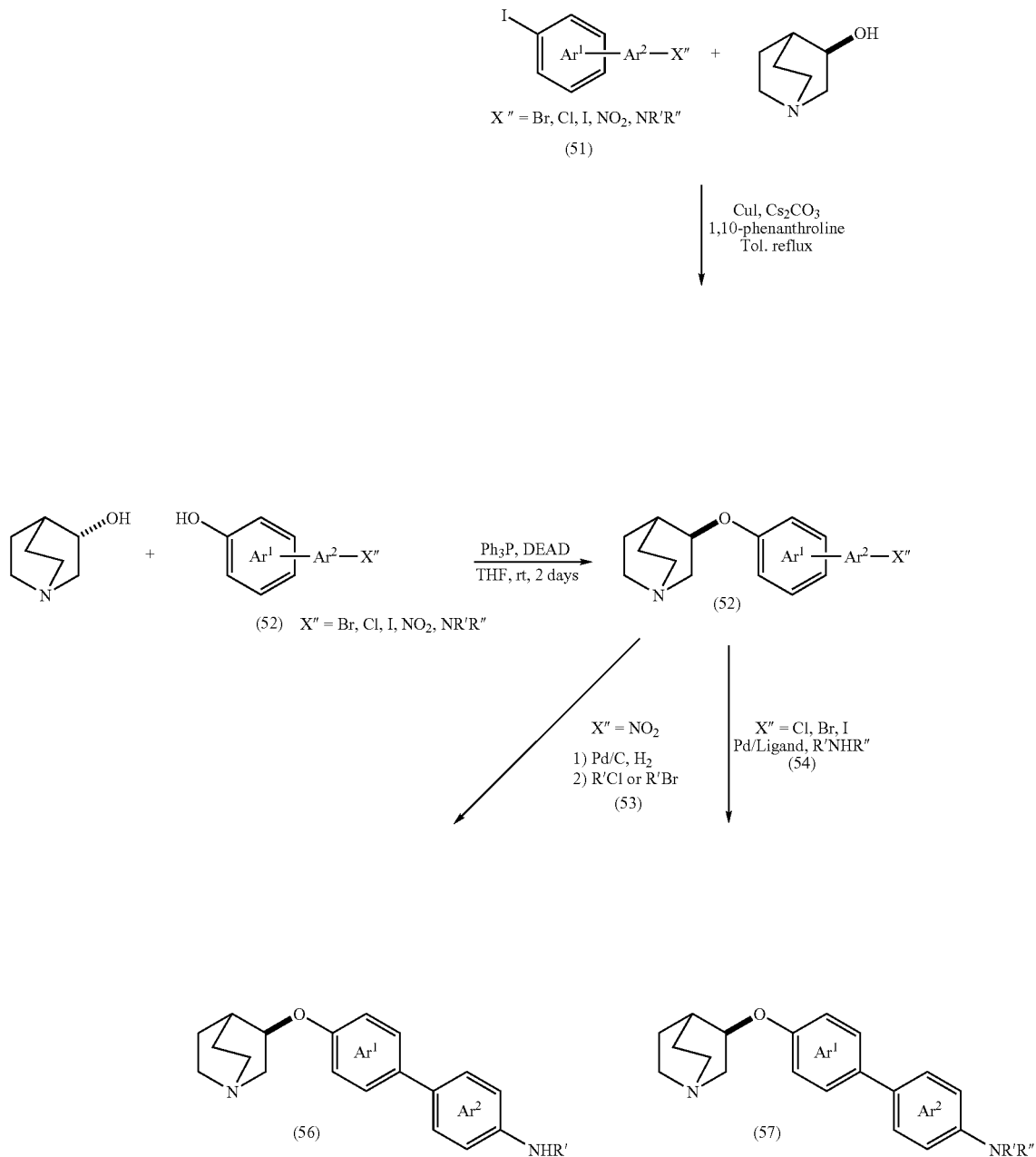

Quinuclidine ethers of formula (56) and (57), wherein Ar¹ is as defined for formula (I) and Ar² is substituted with a group NR⁵R⁶ can be obtained by the methods described in Scheme 8. Compounds of formula (50) can be treated with 3-quinuclidinol in the presence of a phosphine, for example triphenylphosphine, and diethyl azodicarboxylate to provide compounds of formula (52). Alternatively, compounds of formula (51), wherein X" is bromide, chloride, or iodide, can be reacted with CuI, Cs₂CO₃ in 1,10-phenanthroline as described in Org. Lett. 2002, 4, 973, to provide a desired compound of formula (52). Compounds of formula (52), wherein X" is NO₂, can be reduced with hydrogen in the presence of a palladium catalyst and reacted with a chloride or bromide of a desired R group of formula (53), wherein R' is hydrogen, alkyl, aryl, alkycarbonyl, alkoxycarbonyl, arylcarbonyl, or aryloxycarbonyl, to provide compounds of formula (56). Compounds of formula (52), wherein X" is bromide, chloride, or iodide, can be treated with a compound R'NHR" of formula (54), wherein R' and R" are as previously described for R' in compounds of formula (53), to provide a corresponding compound of formula (57).

Scheme 9

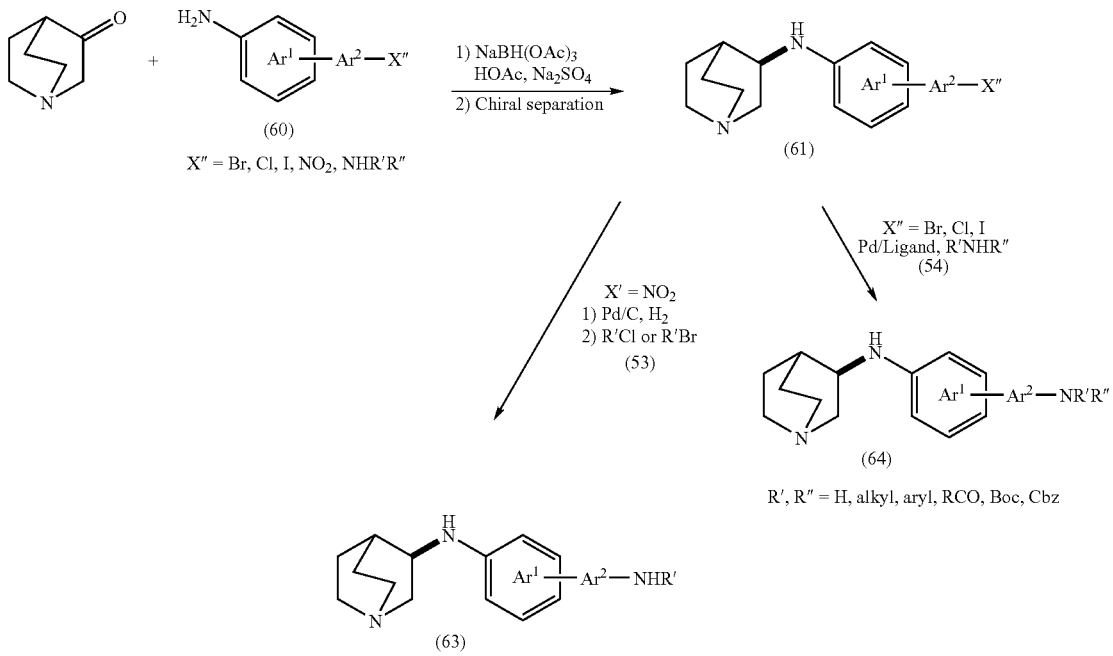

Compounds of formulas (63), and (64) can be prepared as shown in Scheme 9. 3-Quinuclidinone and a halobiarylamine of formula (60), wherein X' is bromide, chloride, or iodide, can be treated with sodium triacetate borohydride and Na₂SO₄ in acetic acid to provide a compound of formula (61) as described in Tetrahedron Lett. 1996, 37, 6045. Compounds of formula (61), wherein X' is bromide, chloride, or iodide, can be treated with a compound R'NHR" of formula (54), wherein R' and R" are as previously described for R' in compounds of formula (53), to provide a corresponding compound of formula (64). Compounds of formula (61), wherein X is NO₂, can be reduced with hydrogen in the presence of a palladium catalyst and reacted with a chloride or bromide of a desired R' group of formula (53), wherein R' is hydrogen, alkyl, aryl, alkycarbonyl, alkoxycarbonyl, arylcarbonyl, or aryloxycarbonyl, to provide compounds of formula (63).

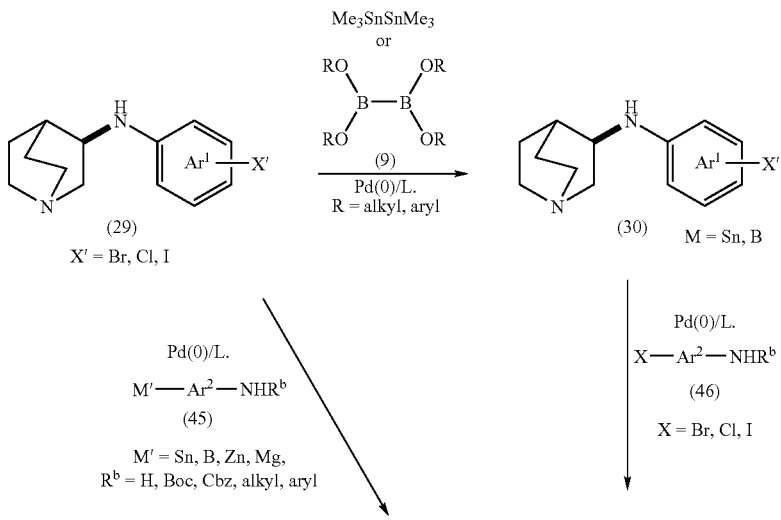

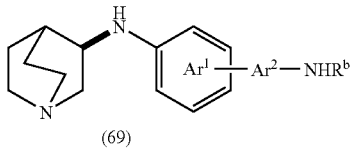

Compounds of formula (69), wherein X is —NH—, $R^3$ is $NHR^b$, and $Ar^1$, $Ar^2$ are defined as in compounds of formula (I), can be prepared as shown in Scheme 10. Compounds of formula (29) obtained as shown in Scheme 7 can be treated with a metal of the desired amino-substituted $Ar^2$ group, as described for compounds of formula (I), of formula (45) to provide compounds of formula (69). Compounds of formula (29) also can be treated with a hexamethylditin or diboron reagent of formula (9), such as bis(pinacolato)diboron and bis(catecholato)diboron, in the presence of a palladium catalyst to provide the corresponding tin or boronic acid of formula (30), which is reacted with a desired halide of an amine-substituted fused bicycloheterocycle represented by $Ar^2$ of formula (46), wherein X' is bromide, chloride, or iodide, to provide compounds of formula (69).

Quinuclidine biarylsulfides of formula (72) and (73), wherein $Ar^1$ is as defined for formula (I) and $Ar^2$ is substituted with a group NR'R" can be obtained by the methods described in Scheme 11. 3-Chloroquinuclidine can be reacted with a halobiarylthiol of formula (70), wherein X" is bromide, chloride, iodide, $NO_2$, or NHR'R", as described in Tetrahedron Lett. 1996, 37, 6045, to provide a compound of formula (71). Compounds of formula (71), wherein X" is $NO_2$, can be reduced with hydrogen in the presence of a palladium catalyst and reacted with a chloride or bromide of a desired R' group of formula (53), wherein R' is hydrogen, alkyl, aryl, alkycarbonyl, alkoxycarbonyl, arylcarbonyl, or aryloxycarbonyl, to provide compounds of formula (72). Compounds of formula (71), wherein X" is bromide, chloride, or iodide, can be treated with a compound R'NHR" of Scheme 11

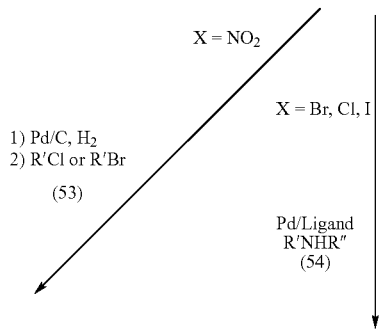

formula (54), wherein R' and R" are as previously described for R' in compounds of formula (53), to provide a corresponding compound of formula (73).

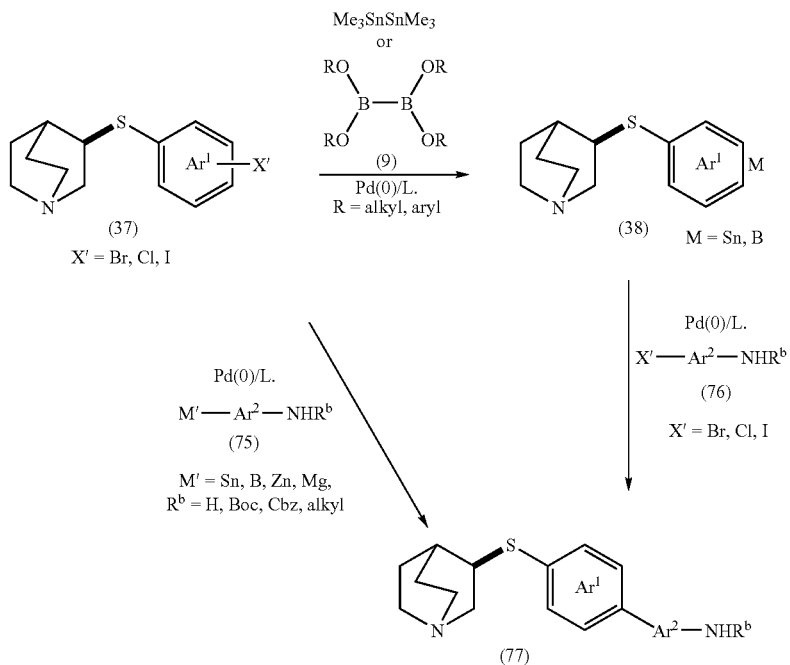

Compounds of formula (77), wherein X is S, $R^3$ is $NHR^b$, and $Ar^1$, $Ar^2$ are defined as in compounds of formula (I) can be prepared as shown in Scheme 12. Compounds of formula (37) obtained as shown in Scheme 5 can be treated with a metal of the desired amino-substituted $Ar^2$ group, as described for compounds of formula (I), of formula (75) to provide compounds of formula (77). Compounds of formula (37) also can be treated with a hexamethylditin or diboron reagent of formula (9), such as bis(pinacolato)diboron and bis(catecholato)diboron, in the presence of a palladium catalyst to provide the corresponding tin or boronic acid of formula (38), which is reacted with a desired halide of an amine-substituted fused bicycloheterocycle represented by $Ar^2$ of formula (76), wherein X' is bromide, chloride, or iodide, to provide compounds of formula (77).

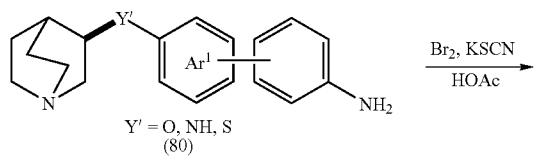

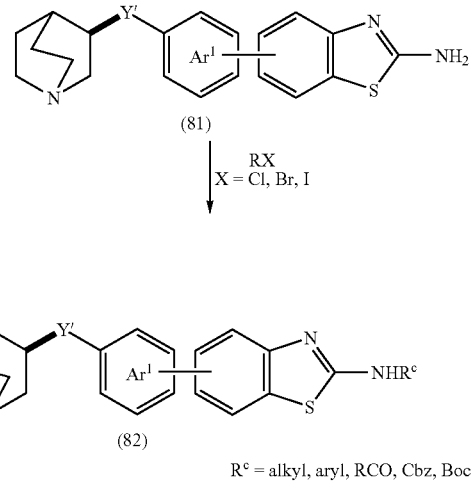

Aminobenzothiazole-substituted quinuclidines of formula (82) can be obtained as shown in Scheme 13. Amino-substituted quinuclidine ethers, thioethers, and amines of formula (80) are obtained by methods described in Schemes 6–12. Compounds of formula (80) are reacted with bromine and KSCN in acetic acid to provide aminobenzothiazole-substituted quinuclidines of formula (81). Compounds of formula (81) can be further treated with the halide of a desired $R^c$ group, wherein $R^c$ as defined for $R^5$ or $R^6$ in compounds of formula (I) to provide the desired aminobenzothiazole-substituted quinuclidine derivative.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Methods of the Invention

Compounds and compositions of the invention are useful for modulating the effects of nAChRs, and more particularly α7 nAChRs. In particular, the compounds and compositions of the invention can be used for treating and preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen.

The compounds of the invention, including but not limited to those specified in the examples, possess an affinity for nAChRs, and more particularly α7 nAChRs. As α7 nAChRs ligands, the compounds of the invention can be useful for the treatment and prevention of a number of α7 nAChR-mediated diseases or conditions.

For example, α7 nAChRs have been shown to play a significant role in enhancing cognitive function, including aspects of learning, memory and attention (Levin, E. D., J.

Neurobiol. 53: 633–640, 2002). As such, α7 ligands are suitable for the treatment of cognitive disorders including, for example, attention deficit disorder, attention deficit hyperactivity disorder (ADHD), Alzheimer's disease (AD), mild cognitive impairment, senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the neuroprotective effects of nicotine both in vitro (Jonnala, R. B. and Buccafusco, J. J., J. Neurosci. Res. 66: 565–572, 2001) and in vivo (Shimohama, S. et al., Brain Res. 779: 359–363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734–4739, 2001). The activation of α7 nAChRs has been shown to block this neurotoxicity (Kihara, T. et al., J. Biol. Chem. 276: 13541–13546, 2001). As such, selective ligands that enhance α7 activity can counter the deficits of Alzheimer's and other neurodegenerative diseases.

Schizophrenia is a complex disease that is characterized by abnormalities in perception, cognition, and emotions. Significant evidence implicates the involvement of α7 nAChRs in this disease, including a measured deficit of these receptors in post-mortem patients (Leonard, S. Eur. J. Pharmacol. 393: 237–242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189–202, 1998; Stevens, K. E. et al., Psychopharmacology 136: 320–327, 1998). Thus, α7 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833–839, 2001). Improved angiogenesis has been shown to involve activation of the α7 nAChR (Heeschen, C. et al, J. Clin. Invest. 110: 527–536, 2002). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin, M. and Changeux, J.-P. PNAS 98:2803–2807, 2001). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384–388, 2003). Therefore, selective α7 ligands demonstrate potential for treating conditions involving inflammation and pain.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reproduct. 68: 1348–1353 2003). Consequently, selective α7 agents demonstrate utility for treating fertility disorders.

Compounds of the invention are particularly useful for treating and preventing a condition or disorder affecting cognition, neurodegeneration, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477–501, 2001). Such cognitive deficit has been linked to dysfunction of the nicotinic cholinergic system, in particular with decreased activity at α7 receptors. (Friedman, J. I. et al., Biol Psychiatry, 51: 349–357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 mg/kg body weight to about 1 g/kg body weight. More preferable doses can be in the range of from about 0.10 mg/kg body weight to about 100 mg/kg body weight. If desired, the effective daily dose can be divided into multiple doses for purposes of administration. Consequently, single dose compositions may contain such amounts or submultiples thereof to make up the daily dose.

The compounds and processes of the invention will be better understood by reference to the following examples and reference examples, which are intended as an illustration of and not a limitation upon the scope of the invention.

EXAMPLES

Example 1

3-[4-(1-azabicyclo[2.2.2]oct-3-yloxy)phenyl]-1H-indole

Example 1A 3-(4-iodophenoxy)quinuclidine

Under $N_2$, the mixture of 3-hydroxy quinuclidine (Aldrich, 2.54 g, 20 mmol), 1,4-diiodobenzene (Aldrich, 7.9 g, 24 mmol), CuI (Strem Chemicals, 0.38 g, 2 mmol) and 1,10-phenanthroline (Aldrich, 0.72 g, 4 mmol) in toluene (anhydrous, Aldrich, 50 mL) was stirred at 110° C. for 40 h. After the reaction went to completion, the reaction mixture was diluted with chloroform (100 mL) and washed with water (2×10 mL). The organic solution was concentrated and the title compound was purified by chromatography ($SiO_2$, $CH_2Cl_2$:MeOH:$NH_3.H_2O$, 90:10:1, $R_f$ 0.20) as oil (3.7 g, yield, 56%). $^1$H NMR (300 MHz, $CD_3OD$) δ 1.40–1.56 (m, 1H), 1.64–1.80 (m, 2H), 1.90–2.08 (m, 1H), 2.10–2.21 (m, 1H), 2.60–3.00 (m, 5H), 3.34–3.40 (m, 1H), 4.46 (m, 1H), 6.73 (d, J=8.8 Hz, 2H), 7.56 (d, J=8.8, Hz, 2H), ppm. MS (DCl/$NH_3$) m/z 330 (M+H)$^+$.

Example 1B

3-[4-(1-azabicyclo[2.2.2]oct-3-yloxy)phenyl]-1H-indole

The mixture of the product of Example 1A (330 mg, 1 mmol), N-(2-ethynyl-phenyl)-2,2,2-trifluoro-acetamide (ref. Tetrahedron Lett. 1992, 33, 3915.; 280 mg, 1.3 mmol), $Pd_2(dba)_3$ (Aldrich, 19 mg, 0.02 mmol) and $K_2CO_3$ (180 mg, 1.3 mmol) in DMSO (3 mL) was stirred at 40° C. under $N_2$ for 2 hours. The reaction was monitored with TLC. After the reaction was complete, it was cooled down to room temperature and diluted with EtOAc (50 mL). It was then washed with brine (3×5 mL). The organic solution was concentrated and the title product was purified by preparative HPLC (Gilson, column, Symmetry® C-8 7 μm, 40×100 mm. Eluting Solvent, MeCN/$H_2O$ (with 0.2% v. TFA) (v. 90/10 to 10/90 over 20 min.) Flow rate, 75 mL/min., uv, 250 nm) as solid (113 mg, yield, 36%). $^1$H NMR (300 MHz, $CD_3OD$) δ 1.43–1.57 (m, 1H), 1.62–1.89 (m, 2H), 2.01–2.15 (m, 1H), 2.16–2.23 (m, 1H), 2.73–3.03 (m, 5H), 3.28–3.40 (m, 1H), 4.51–4.58 (m, 1H), 6.97 (dt, J=8.8, 2.1 Hz, 1H), 7.03–7.17 (m, 2H), 7.36 (s, 1H), 7.37–7.42 (m, 1H), 7.57 (dt, J=8.8, 2.0 Hz, 2H), 7.81 (dt, J=7.8, 1.2 Hz, 1H) ppm. MS (DCl/$NH_3$) m/z 319 (M+H)$^+$.

Example 1C

3-[4-(1-azabicyclo[2.2.2]oct-3-yloxy)phenyl]-1H-indole hemifumarate

The product of Example 1B (113 mg, 0.36 mmol) was treated with fumaric acid (46 mg, 0.4 mmol) in EtOAc/EtOH (v. 1:1, 4 mL) at ambient temperature for 10 h. The title compound was obtained as solid (131 mg, yield, 89%). $^1$H NMR (300 MHz, $CD_3OD$) δ 1.73–2.13 (m, 3H), 2.23–2.37 (m, 1H), 2.43–2.51 (m, 1H), 3.12–3.43 (m, 5H), 3.64–3.76 (m, 1H), 4.77–4.88 (m, 1H), 6.67 (s, 1.4H), 6.99–7.18 (m, 4H), 7.38 (s, 1H), 7.39–7.43 (m, 1H), 7.61 (dt, J=8.8, 2.0 Hz, 2H), 7.80 (d, J=7.8 Hz, 1H) ppm. MS (DCl/$NH_3$): m/z 319 (M+H)$^+$. Anal. Calculated for $C_{21}H_{22}N_2O.0.85C_4H_4O_4$: C, 70.27; H, 6.14; N, 6.72. Found: C, 70.20; H, 6.35; N, 6.88.

Example 2

4-[4-(1-azabicyclo[2.2.2]oct-3-yloxy)phenyl]-1H-indole

Example 2A

3-[4-(trimethylstannyl)phenoxy]quinuclidine

The mixture of the product from Example 1A (330 mg, 1 mmol), hexamethylditin (Aldrich, 654 mg, 2 mmol) and $Pd(PPh_3)_4$ (Aldrich, 116 mg, 0.1 mmol) in toluene (10 mL) was stirred at 110° C. under $N_2$ for 2 hours. The reaction was monitored with TLC. After the reaction was complete, it was cooled down to room temperature and diluted with EtOAc (50 mL). It was then washed with brine (2×5 mL). The organic solution was concentrated under reduced pressure and the title compound was purified by flash chromatography ($SiO_2$, $CH_2Cl_2$:MeOH:$NH_3.H_2O$, 90:10:1, $R_f$ 0.35) as solid (300 mg, yield, 82%). $^1$H NMR (300 MHz, $CD_3OD$) δ 0.25 (s, 9H), 1.79–2.16 (m, 3H), 2.23–2.36 (m, 1H), 2.45–2.52 (m, 1H), 3.17–3.43 (m, 5H), 3.73–3.83 (m, 1H), 4.84–4.92 (m, 1H), 6.96 (d, J=8.5 Hz, 2H), 7.41 (d, J=8.5 Hz, 2H) ppm. MS (DCl/$NH_3$): m/z 364 (M+H)$^+$, 366 (M+H)$^+$, 368 (M+H)$^+$.

Example 2B

4-[4-(1-azabicyclo[2.2.2]oct-3-yloxy)phenyl]-1H-indole

The product of 2A (300 mg, 0.8 mmol), 4-bromoindole (Aldrich, 196 mg, 1 mmol), $Pd_2(dba)_3$ (Aldrich, 27 mg, 0.03 mmol) and (o-tol.)$_3$P (Aldrich, 27 mg, 0.09 mmol) in DMF (Aldrich, anhydrous, 5 mL) were heated to 80° C. under $N_2$ and stirred overnight. It was then cooled down to room temperature and diluted with EtOAc (50 mL). The mixture was washed with brine (2×5 mL). The organic solution was concentrated under reduced pressure and the title compound was purified by flash chromatography ($SiO_2$, $CH_2Cl_2$:MeOH:$NH_3.H_2O$, 90:10:1, $R_f$ 0.30) as a solid (48 mg, yield, 19%). $^1$H NMR (300 MHz, $CD_3OD$) δ 1.46–1.58 (m, 1H), 1.64–1.91 (m, 2H), 2.01–2.17 (m, 1H), 2.19–2.26 (m, 1H), 2.75–3.03 (m, 5H), 3.32–3.42 (m, 1H), 4.55–4.63 (m, 1H), 6.58 (dd, J=3.4, 1.0 Hz, 1H), 6.98–7.04 (m, 3H), 7.14 (t, J=7.8 Hz, 1H), 7.25 (d, J=3.1 Hz, 1H), 7.33 (dt, J=8.1, 1.0 Hz, 1H), 7.59 (dt, J=9.2, 2.7 Hz, 2H) ppm. MS (DCl/$NH_3$): m/z 319 (M+H)$^+$.

Example 2C

4-[4-(1-azabicyclo[2.2.2]oct-3-yloxy)phenyl]-1H-indole fumarate

The product of Example 2B (48 mg, 0.15 mmol) was treated with fumaric acid (23 mg, 0.2 mmol) in EtOAc/EtOH (v. 1:1, 3 mL) at ambient temperature for 15 h. The title compound was obtained as solid (60.2 mg, yield, 90%). $^1$H NMR (300 MHz, CD$_3$OD) δ 1.82–2.19 (m, 3H), 2.29–2.42 (m, 1H), 2.51–2.58 (m, 1H), 3.16–3.46 (m, 5H), 3.75–3.85 (m, 1H), 4.89–4.96 (m, 1H), 6.56 (dd, J=3.4, 1.0 Hz, 1H), 6.69 (s, 2.2H), 7.02 (dd, J=7.1, 1.0 Hz, 1H), 7.08 (dt, J=8.8, 2.5 Hz, 2H), 7.15 (t, J=7.5 Hz, 1H), 7.26 (d, J=3.4 Hz, 1H), 7.35 (dt, J=8.1, 1.0 Hz, 1H), 7.64 (dt, J=8.8, 2.6 Hz, 2H) ppm. MS (DCI/NH$_3$): m/z 319 (M+H)$^+$. Anal. Calculated for C$_{21}$H$_{22}$N$_2$O.1.12C$_4$H$_4$O$_4$: C, 68.25; H, 5.95; N, 6.25. Found: C, 68.43; H, 5.58; N, 6.20.

Example 3

5-[4-(1-azabicyclo[2.2.2]oct-3-yloxy)phenyl]-1H-indole

Example 3A

5-[4-(1-azabicyclo[2.2.2]oct-3-yloxy)phenyl]-1H-indole

Under N$_2$, the product of Example 1A (329 mg, 1 mmol), 5-indolylboronic acid (Frontier, 193 mg, 1.2 mmol), Pd$_2$(dba)$_3$ (Aldrich, 24 mg, 0.025 mmol), ($^t$Bu$_3$P)$_2$Pd (26 mg, 0.05 mmol), K$_2$CO$_3$ (276 mg, 2 mmol) and KF (80 mg, 1.4 mmol) in THF (8 mL) was stirred at 60° C. overnight. The reaction was monitored with TLC. After the reaction was complete, it was diluted with EtOAc (30 mL) and washed with brine (2×5 mL). The organic solution was concentrated under reduced pressure and the title product was purified by preparative HPLC (Gilson, column, Symmetry® C-8 7 μm, 40×100 mm. Eluting Solvent, MeCN/H$_2$O (with 0.2% v. TFA) (v. 90/10 to 10/90 over 20 min.) Flow rate, 75 mL/min., uv, 250 nm) as solid (80 mg, yield, 25%). $^1$H NMR (300 MHz, CD$_3$OD) δ 1.44–1.58 (m, 1H), 1.62–1.90 (m, 2H), 2.01–2.15 (m, 1H), 2.16–2.24 (m, 1H), 2.74–3.04 (m, 5H), 3.27–3.40 (m, 1H), 4.51–4.59 (m, 1H), 6.46 (dd, J=3.4, 1.1 Hz, 1H), 6.95 (dt, J=8.8, 2.6 Hz, 2H), 7.22 (d, J=3.1 Hz, 1H), 7.31 (dd, J=8.5, 2.0 Hz, 1H), 7.40 (dt, J=8.5, 1.0 Hz, 1H), 7.54 (dt, J=9.2, 2.6 Hz, 2H), 7.71 (dd, J=1.7, 0.7 Hz, 1H) ppm. MS (DCI/NH$_3$): m/z 319 (M+H)$^+$.

Example 3B

5-[4-(1-azabicyclo[2.2.2]oct-3-yloxy)phenyl]-1H-indole fumarate

The product of Example 3A (80 mg, 0.25 mmol) was treated with fumaric acid (29 mg, 0.25 mmol) in EtOAc/EtOH (v. 1:1, 4 mL) at ambient temperature for 10 h. The title compound was obtained as solid (57 mg, yield, 52%). $^1$H NMR (300 MHz, CD$_3$OD) δ 1.78–2.16 (m, 3H), 2.25–2.39 (m, 1H), 2.46–2.54 (m, 1H), 3.14–3.45 (m, 5H), 3.69–3.81 (m, 1H), 4.80–4.89 (m, 1H), 6.46 (dd, J=3.0, 1.0, 1H), 6.68 (s, 2H), 7.02 (dt, J=8.8, 2.5 Hz, 2H), 7.23 (d, J=3.1 Hz, 1H), 7.31 (dd, J=8.5, 2.0 Hz, 1H), 7.43 (dt, J=8.4, 0.8 Hz, 1H), 7.58 (dt, J=9.2, 2.6 Hz, 2H), 7.71 (dd, J=1.7, 1.0 Hz, 1H) ppm. MS (DCI/NH$_3$): m/z 319 (M+H)$^+$. Anal. Calculated for C$_{21}$H$_{22}$N$_2$O.C$_4$H$_4$O$_4$: C, 69.11; H, 6.03; N, 6.45. Found: C, 69.23; H, 5.81; N, 6.59.

Example 4

5-{4-[(3R)-1-azabicyclo[2.2.2]oct-3-yloxy]phenyl}-1H-indole

Example 4A

(3R)-3-Quinuclidinol (3R)-3-Quinuclidinol hydrochloride (Aldrich, 20 g, 12.2 mmol) was treated with NaOH aqueous solution (20%, 50 mL) at ambient temperature for 10 min. It was then extracted with CHCl$_3$/$^i$PrOH (v. 10:1, 3×200 mL). The extracts were combine, washed with brine (50 mL) and dried over MgSO$_4$. The drying agents were removed by filtration and the filtrates was concentrated under reduced pressure to give the title compound as white solid (15.5 g, yield, 99%). $^1$H NMR (300 MHz, CD$_3$OD) δ 1.36–1.50 (m, 1H), 1.52–1.60 (m, 1H), 1.76–1.85 (m, 2H), 1.90–2.05 (m, 1H), 2.50–2.95 (m, 5H), 3.10 (ddd, J=14.2, 8.4, 2.3 Hz, 1H), 3.82–3.88 (m, 1H) ppm. MS (DCI/NH$_3$): m/z 128 (M+H)$^+$.

Example 4B

(3R)-3-(4-bromophenoxy)quinuclidine

The product of Example 4A (1.27 g, 10 mmol) was coupled with 1-iodo-4-bromobenzene (Aldrich, 2.83 g, 10 mol) according to the procedure of Example 1A. The title product was purified by chromatography (SiO$_2$, CH$_2$Cl$_2$:MeOH:NH$_3$.H$_2$O, 90:10:1, R$_f$. 0.30) as solid (400 mg, yield, 14%). $^1$H NMR (300 MHz, CD$_3$OD) δ 1.41–1.54 (m, 1H), 1.59–1.73 (m, 1H), 1.73–1.86 (m, 1H), 1.92–2.06 (m, 1H), 2.09–2.17 (m, 1H), 2.71–2.97 (m, 5H), 3.24–3.34 (m, 1H), 4.45–4.52 (m, 1H), 6.83 (dt, J=9.2, 2.6 Hz, 2H), 7.37 (dt, J=9.2, 2.7 Hz, 2H) ppm. MS (DCI/NH$_3$): m/z 282 (M+H)$^+$, 284 (M+H)$^+$.

Example 4C

5-{4-[(3R)-1-azabicyclo[2.2.2]oct-3-yloxy]phenyl}-1H-indole

The product of 4C (282 mg, 1 mmol) coupled with 5-indolylboronic acid (Frontier, 190 mg, 1.2 mmol) according to the procedure of Example 3A. The title product was purified by chromatography (SiO$_2$, CH$_2$Cl$_2$:MeOH:NH$_3$.H$_2$O, 90:10:1, R$_f$. 0.35) as solid (50 mg, yield, 16%). $^1$H NMR (300 MHz, CD$_3$OD) δ 1.44–1.58 (m, 1H), 1.62–1.90 (m, 2H), 2.01–2.15 (m, 1H), 2.16–2.24 (m, 1H), 2.74–3.04 (m, 5H), 3.27–3.40 (m, 1H), 4.51–4.59 (m, 1H), 6.46 (dd, J=3.4, 1.1 Hz, 1H), 6.95 (dt, J=8.8, 2.6 Hz, 2H), 7.22 (d, J=3.1 Hz, 1H), 7.31 (dd, J=8.5, 2.0 Hz, 1H), 7.40 (dt, J=8.5, 1.0 Hz, 1H), 7.54 (dt, J=9.2, 2.6 Hz, 2H), 7.71 (dd, J=1.7, 0.7 Hz, 1H) ppm. MS (DCI/NH$_3$): m/z 319 (M+H)$^+$.

Example 4D

5-{4-[(3R)-1-azabicyclo[2.2.2]oct-3-yloxy]phenyl}-1H-indole fumarate

The product of Example 4C (50 mg, 0.25 mmol) was treated with fumaric acid (29 mg, 0.25 mmol) in EtOAc/EtOH (v. 1:1, 4 mL) at ambient temperature for 10 h. The title compound was obtained as solid (56.9 mg, yield, 52%). $^1$H NMR (300 MHz, CD$_3$OD) δ 1.78–2.16 (m, 3H), 2.25–2.39 (m, 1H), 2.46–2.54 (m, 1H), 3.14–3.45 (m, 5H), 3.69–3.81 (m, 1H), 4.80–4.89 (m, 1H), 6.46 (dd, J=3.0, 1.0, 1H), 6.68 (s, 2.2H), 7.02 (dt, J=8.8, 2.5 Hz, 2H), 7.23 (d, J=3.1 Hz, 1H), 7.31 (dd, J=8.5, 2.0 Hz, 1H), 7.43 (dt, J=8.4, 0.8 Hz, 1H), 7.58 (dt, J=9.2, 2.6 Hz, 2H), 7.71 (dd, J=1.7, 1.0 Hz, 1H) ppm. MS (DCl/NH$_3$): m/z 319 (M+H)$^+$. Anal. Calculated for C$_{21}$H$_{22}$N$_2$O.1.14C$_4$H$_4$O$_4$: C, 68.11; H, 5.94; N, 6.21. Found: C, 68.12; H, 6.04; N, 6.18.

Example 5

6-[4-(1-azabicyclo[2.2.2]oct-3-yloxy)phenyl]-1H-indole

Example 5A

6-[4-(1-azabicyclo[2.2.2]oct-3-yloxy)phenyl]-1H-indole

The product of Example 2A (300 mg, 0.8 mmol) was coupled with 6-bromoindole (Aldrich, 196 mg, 1 mmol) according to the procedure in 2B. The title compound was purified by chromatography (SiO$_2$, CH$_2$Cl$_2$:MeOH:NH$_3$.H$_2$O, 90:10:1, R$_f$ 0.20) as a solid (30 mg, yield, 12%). $^1$H NMR (300 MHz, CD$_3$OD) δ 1.45–1.58 (m, 1H), 1.64–1.90 (m, 2H), 2.01–2.15 (m, 1H), 2.17–2.24 (m, 1H), 2.75–3.04 (m, 5H), 3.30–3.42 (m, 1H), 4.53–4.61 (m, 1H), 6.43 (dd, J=3.1, 0.7 Hz, 1H), 6.97 (dt, J=8.8, 2.6 Hz, 2H), 7.21–7.27 (m, 2H), 7.52–7.60 (m, 4H) ppm. MS (DCl/NH$_3$): m/z 319 (M+H)$^+$.

Example 5B

6-[4-(1-azabicyclo[2.2.2]oct-3-yloxy)phenyl]-1H-indole fumarate

The product of Example 5A (30 mg, 0.1 mmol) was treated with fumaric acid (12 mg, 0.1 mmol) in EtOAc/EtOH (v. 1:1, 2 mL) at ambient temperature for 15 h. The title compound was obtained as solid (38.4 mg, yield, 79%). $^1$H NMR (300 MHz, CD$_3$OD) δ 1.80–2.19 (m, 3H), 2.27–2.40 (m, 1H), 2.48–2.56 (m, 1H), 3.17–3.63 (m, 5H), 3.72–3.83 (m, 1H), 4.80–4.88 (m, 1H), 6.43 (dd, J=3.1, 0.7 Hz, 1H), 6.68 (s, 2H), 7.04 (dt, J=8.8, 2.5 Hz, 2H), 7.21–7.27 (m, 2H), 7.53–7.65 (m, 4H) ppm. MS(DCl/NH$_3$): m/z 319 (M+H)$^+$. Anal. Calcd. for C$_{19}$H$_{20}$N$_4$O.1.3C$_4$H$_4$O$_4$: C, 67.05; H, 5.84; N, 5.97. Found: C, 67.15; H, 5.99; N, 5.95.

Example 6

2-[4-(1-azabicyclo[2.2.2]oct-3-yloxy)phenyl]-1H-indole

Example 6A

3-(4-ethynylphenoxy)quinuclidine

Under N$_2$, the mixture of the product from Example 1A (800 mg, 2.4 mmol), trimethylsilylacetylene (Aldrich, 392 mg, 4 mmol), Pd(PPh$_3$)$_4$ (Aldrich, 29 mg, 0.025 mmol) and CuI (Strem Chemicals, 10 mg, 0.05 mmol) in DMF (10 mL) was stirred at ambient temperature overnight. DMF then was removed under reduced pressure. The residue was treated with tetrabutyl ammonium fluoride (Aldrich, in THF, 1M, 5 mL) at room temperature for 3 h. The reaction was monitored with TLC. After the reaction was complete, it was diluted with EtOAc (50 mL) and washed with brine (2×10 mL). The organic solution was concentrated and the title compound was purified by chromatography (SiO$_2$, CH$_2$Cl$_2$:MeOH:NH$_3$.H$_2$O, 90:10:1, R$_f$ 0.30) as a solid (560 mg, yield, 99%). $^1$H NMR (300 MHz, CD$_3$OD) δ 1.42–1.54 (m, 1H), 1.61–1.87 (m, 2H), 1.93–2.07 (m, 1H), 2.10–2.18 (m, 1H), 2.71–3.00 (m, 5H), 3.19–3.37 (m, 2H), 4.49–4.56 (m, 1H), 6.86 (d, J=8.8 Hz, 2H), 7.37 (d, J=8.8 Hz, 2H) ppm. MS (DCl/NH$_3$): m/z 228 (M+H)$^+$.

Example 6B

2,2,2-trifluoro-N-(2-iodophenyl)acetamide

2-Iodo-phenylamine (Aldrich, 1.09 g, 5 mmol) was treated with trifluoroacetic anhydride (Aldrich, 1.26 g, 6 mmol) and 2,6-di-tert-butyl-4-methyl-pyridine (Aldrich, 1.23 g, 6 mmol) in CH$_2$Cl$_2$ (10 mL) at room temperature overnight. It was then quenched with with water (5 mL) and extracted with EtOAc (3×10 mL). The extracts were combined and washed with brine (5 mL). The organic solution was concentrated and the title compound was purified by flash chromatography (SiO$_2$, Hexanes/EtOAc, 80:20, R$_f$ 0.50) as a solid (1.1 g, yield, 70%). $^1$H NMR (300 MHz, CD$_3$OD) δ 7.07–7.12 (m, 1H), 7.39–7.47 (m, 2H), 7.95 (dd, J=7.8, 1.3 Hz, 1H) ppm. MS (DCl): m/z 316 (M+H)$^+$.

Example 6C

2-[4-(1-azabicyclo[2.2.2]oct-3-yloxy)phenyl]-1H-indole

Under N$_2$, the mixture of product from Example 6A (114 mg, 0.5 mmol), the product from Example 6B (157 mg, 0.5 mmol), CuI (Strem Chemicals, 14 mg, 0.075 mmol), PPh$_3$ (Aldrich, 39 mg, 0.15 mmol) and K$_3$PO$_4$ (212 mg, 1 mmol) in dioxane (5 mL) was stirred at 80° C. for 20 h. After the reaction was complete, it was diluted with EtOAc (30 mL) and washed with brine (2×5 mL). The organic solution was concentrated under reduced pressure and the title compound was purified by chromatography (SiO$_2$, CH$_2$Cl$_2$:MeOH:NH$_3$.H$_2$O, 90:10:1, R$_f$ 0.30) as solid (70 mg, yield, 44%). $^1$H NMR (300 MHz, CD$_3$OD) δ 1.45–1.59 (m, 1H), 1.65–1.91 (m, 2H), 2.00–2.14 (m, 1H), 2.17–2.24 (m, 1H), 2.75–3.01 (m, 5H), 3.31–3.42 (m, 1H), 4.54–4.62 (m, 1H), 6.66 (d, J=0.7 Hz, 1H), 6.93–7.00 (m, 3H), 7.01–7.08 (m, 1H), 7.35 (dq, J=8.2, 1.0 Hz, 1H), 7.48 (dq, J=7.8, 0.7 Hz, 1H), 7.71 (dt, J=8.8, 2.6 Hz, 2H) ppm. MS (DCl/NH$_3$): m/z 319 (M+H)$^+$.

Example 6D

2-[4-(1-azabicyclo[2.2.2]oct-3-yloxy)phenyl]-1H-indole fumarate

The product of Example 6C (70 mg, 0.22 mmol) was treated with fumaric acid (29 mg, 0.25 mmol) in EtOAc/EtOH (v. 1:1, 3 mL) at ambient temperature for 10 h. The title compound was obtained as solid (87 mg, yield, 89%). $^1$H NMR (300 MHz, CD$_3$OD) δ 1.81–2.18 (m, 3H), 2.25–2.39 (m, 1H), 2.48–2.56 (m, 1H), 3.19–3.48 (m, 5H), 3.73–3.85 (m, 1H), 4.86–4.93 (m, 1H), 6.65–6.80 (m, 2H), 6.94–7.10 (m, 4H), 7.36 (dd, J=8.1, 0.7 Hz, 1H), 7.49 (dt, J=7.8, 1.0 Hz, 1H), 7.75 (dq, J=9.2, 2.4 Hz, 2H) ppm. MS (DCl/NH$_3$): m/z 319 (M+H)$^+$. Anal. Calculated for C$_{21}$H$_{22}$N$_2$O.1.1C$_4$H$_4$O$_4$: C, 68.39; H, 5.96; N, 6.28. Found: C, 68.10; H, 6.22; N, 6.25.

Example 7

5-[6-(1-azabicyclo[2.2.2]oct-3-yloxy)pyridazin-3-yl]-1H-indole

Example 7A

3-[(6-chloropyridazin-3-yl)oxy]quinuclidine

3-Quinuclidinol (Aldrich, 508 mg, 4 mmol) was treated with ʹBuOK (Aldrich, 448 mg, 4 mmol) in THF (20 mL) at ambient temperature for 1 hour. 3,6-Dichloropyradazine (Aldrich, 740 mg, 5 mmol) was then added. The mixture was stirred at ambient temperature for additional 1 h. The reaction was monitored with TLC. After the reaction was complete, it was concentrated under reduced pressure. The residue was dissolved in $CHCl_3$/ʹPrOH (v. 10:1, 50 mL) and washed with brine (2×5 mL). The organic solution was concentrated under reduced pressure and the title compound was purified by chromatography ($SiO_2$, $CH_2Cl_2$:MeOH:$NH_3 \cdot H_2O$, 90:10:1, $R_f$ 0.45) as a solid (780 mg, yield, 82%). $^1H$ NMR (300 MHz, $CD_3OD$) δ 1.48–1.61 (m, 1H), 1.65–1.90 (m, 2H), 1.94–2.08 (m, 1H), 2.23–2.31 (m, 1H), 2.73–3.01 (m, 5H), 3.37–3.48 (m, 1H), 5.18–5.27 (m, 1H), 7.23 (d, J=9.2 Hz, 1H), 7.65 (d, J=9.2 Hz, 1H) ppm. MS (DCl/$NH_3$): 240 (M+H)$^+$.

Example 7B

5-[6-(1-azabicyclo[2.2.2]oct-3-yloxy)pyridazin-3-yl]-1H-indole

The product of Example 7A (200 mg, 0.8 mmol) was coupled with 5-indolylboronic acid (161 mg, 1 mmol) according to the procedure of Example 3A. The title product was purified by preparative HPLC (Gilson, column, Symmetry® C-8 7 μm, 40×100 mm. Eluting Solvent, MeCN/$H_2O$ (with 0.2% v. TFA) (v. 90/10 to 10/90 over 20 min.) Flow rate, 75 mL/min., uv, 250 nm) as solid (35 mg, yield, 14%). $^1H$ NMR (300 MHz, $CD_3OD$) δ 1.50–1.65 (m, 1H), 1.70–1.93 (m, 2H), 2.00–2.16 (m, 1H), 2.29–2.37 (m, 1H), 2.78–3.05 (m, 5H), 3.44–3.55 (m, 1H), 5.26–5.35 (m, 1H), 6.56 (dd, J=3.3, 1.1 Hz, 1H)), 7.25 (d, J=9.2 Hz, 1H), 7.31 (d, J=3.4 Hz, 1H), 7.51 (d, J=8.8 Hz, 1H), 7.73 (dd, J=8.5, 1.7 Hz, 1H), 8.08 (d, J=9.5 Hz, 1H), 8.14 (d, J=1.7 Hz, 1H) ppm. MS (DCl/$NH_3$): m/z 321 (M+H)$^+$.

Example 7C

5-[6-(1-azabicyclo[2.2.2]oct-3-yloxy)pyridazin-3-yl]-1H-indole hemifumarate

The product of Example 7B (35 mg, 0.11 mmol) was treated with fumaric acid (23 mg, 0.2 mmol) in EtOAc/EtOH (v. 1:1, 3 mL) at ambient temperature for 10 h. The title compound was obtained as solid (42 mg, yield, 99%). $^1H$ NMR (300 MHz, $CD_3OD$) δ 1.76–1.91 (m, 1H), 1.92–2.13 (m, 2H), 2.22–2.36 (m, 1H), 2.51–2.59 (m, 1H), 3.12–3.40 (m, 5H), 3.77–3.88 (m, 1H), 5.42–5.51 (m, 1H), 6.56 (dd, J=2.0, 1.0 Hz, 1H), 6.67 (s, 1H), 7.27–7.33 (m, 2H), 7.52 (dt, J=8.5, 1.0 Hz, 1H), 7.74 (dd, J=8.8, 1.7 Hz, 1H), 8.10–8.16 (m, 2H) ppm. MS (DCl/$NH_3$): m/z 321 (M+H)$^+$. Anal. Calculated for $C_{19}H_{20}N_4O \cdot 0.55C_4H_4O_4$: C, 66.27; H, 5.82; N, 14.58. Found: C, 66.12; H, 5.53; N, 14.63.

Example 8

4-[6-(1-azabicyclo[2.2.2]oct-3-yloxy)pyridazin-3-yl]-1H-indole

Example 8A

4-[6-(1-azabicyclo[2.2.2]oct-3-yloxy)pyridazin-3-yl]-1H-indole

Under $N_2$, the mixture of Example 7A (168 mg, 0.7 mmol), 4-(4,4,5,5-tetramethyl-[1,3,2]dioxaborolan-2-yl)-1H-indole (ref. WO02055517, 170 mg, 0.7 mmol), $Pd_2(dba)_3$ (Aldrich, 19 mg, 0.02 mmol), 1,3-bis(2,6-iso-propylphenyl)imidazolium chloride (Strem Chemicals, 26 mg, 0.06 mmol) and aqueous $Na_2CO_3$ (2 M, 1 mL) in toluene (10 mL) was stirred at 110° C. overnight, After the reaction was complete, it was cooled down to room temperature and diluted with EtOAc (30 mL). The mixture was then washed with brine (2×5 mL) and the title compound was purified by chromatography ($SiO_2$, $CH_2Cl_2$:MeOH:$NH_3 \cdot H_2O$, 90:10:1, $R_f$ 0.10) as solid (45 mg, yield, 20%). $^1H$ NMR (300 MHz, $CD_3OD$) δ 1.51–1.65 (m, 1H), 1.70–1.93 (m, 2H), 2.01–2.16 (m, 1H), 2.31–2.39 (m, 1H), 2.78–3.09 (m, 5H), 3.45–3.56 (m, 1H), 5.30–5.38 (m, 1H), 6.78 (dd, J=3.4, 1.0 Hz, 1H), 7.25 (t, J=7.8 Hz, 1H), 7.30 (d, J=9.5 Hz, 1H), 7.36 (d, J=3.1 Hz, 1H), 7.40 (dd, J=7.5, 1.0 Hz, 1H), 7.52 (dt, J=8.1, 1.0 Hz, 1H), 8.07 (d, J=9.2 Hz, 1H) ppm. MS (DCl/$NH_3$): m/z 321 (M+H)$^+$.

Example 8B

4-[6-(1-azabicyclo[2.2.2]oct-3-yloxy)pyridazin-3-yl]-1H-indole fumarate

The product of Example 8A (45 mg, 0.14 mmol) was treated with fumaric acid (23 mg, 0.2 mmol) in EtOAc/EtOH (v. 1:1, 3 mL) at ambient temperature for 10 h. The title compound was obtained as solid (56 mg, yield, 85%). $^1H$ NMR (300 MHz, $CD_3OD$) δ 1.90–2.23 (m, 3H), 2.33–2.48 (m, 1H), 2.62–2.70 (m, 1H), 3.21–3.54 (m, 5H), 3.92–4.03 (m, 1H), 5.54–5.62 (m, 1H), 6.69 (s, 2.5H), 6.78 (dd, J=3.4, 1.0 Hz, 1H), 7.26 (t, J=7.5 Hz, 1H), 7.35–7.44 (m, 3H), 7.55 (dt, J=8.1, 1.1 Hz, 1H), 8.13 (d, J=9.2 Hz, 1H) ppm. MS (DCl/$NH_3$): m/z 321 (M+H)$^+$. Anal. Calculated for $C_{19}H_{20}N_4O \cdot 1.3C_4H_4O_4$: C, 61.67; H, 5.39; N, 11.89. Found: C, 61.49; H, 5.52; N, 12.17.

Example 9

5-{6-[(3R)-1-azabicyclo[2.2.2]oct-3-yloxy]pyridazin-3-yl}-1H-indole

Example 9A

(3R)-3-[(6-chloropyridazin-3-yl)oxy]quinuclidine

The product of Example 4A (635 mg, 5 mmol) was coupled with 3,6-dichloropyridazine (Aldrich, 925 mg, 6.25 mmol) according to the procedure of Example 7A. The title compound was purified by chromatography ($SiO_2$, $CH_2Cl_2$:MeOH:$NH_3 \cdot H_2O$, 90:10:1, $R_f$ 0.45) as solid (750 mg, yield, 63%). $^1H$ NMR (300 MHz, $CD_3OD$) δ 1.54–1.68 (m, 1H), 1.71–1.95 (m, 2H), 2.00–2.14 (m, 1H), 2.28–2.36 (m, 1H), 2.83–3.08 (m, 5H), 3.44–3.56 (m, 1H), 5.23–5.30 (m, 1H), 7.24 (d, J=9.2 Hz, 1H), 7.66 (d, J=9.2 Hz, 1H) ppm. MS (DCl/$NH_3$): 240 (M+H)$^+$.

Example 9B

5-{6-[(3R)-1-azabicyclo[2.2.2]oct-3-yloxy]pyridazin-3-yl}-1H-indole

The product of Example 9A (480 mg, 2 mmol) was coupled with 5-indolylboronic acid (Frontier, 403 mg, 2.5 mmol) according to the procedure of Example 3A. The title product was purified by preparative HPLC (Gilson, column, Symmetry® C-8 7 μm, 40×100 mm. Eluting Solvent, MeCN/H$_2$O (with 0.2% v. TFA) (v. 90/10 to 10/90 over 20 min.) Flow rate, 75 mL/min., uv, 250 nm) as solid (240 mg, yield, 38%). $^1$H NMR (300 MHz, CD$_3$OD) δ 1.49–1.64 (m, 1H), 1.68–1.93 (m, 2H), 2.00–2.15 (m, 1H), 2.28–2.36 (m, 1H), 2.76–3.05 (m, 5H), 3.43–3.55 (m, 1H), 5.26–5.34 (m, 1H), 6.56 (dd, J=3.4, 1.0 Hz, 1H), 7.25 (d, J=9.2 Hz, 1H), 7.31 (d, J=3.1 Hz, 1H), 7.50 (d, J=8.5 Hz, 1H), 7.74 (dd, J=8.5, 1.7 Hz, 1H), 8.08 (d, J=9.5 Hz, 1H), 8.14 (d, J=1.4 Hz, 1H) ppm. MS (DCl/NH$_3$): m/z 321 (M+H)$^+$.

Example 9C

5-{6-[(3R)-1-azabicyclo[2.2.2]oct-3-yloxy]pyridazin-3-yl}-1H-indole fumarate

The product of Example 9B (240 mg, 0.75 mmol) was treated with fumaric acid (93 mg, 0.8 mmol) in EtOAc/EtOH (v. 1:1, 10 mL) at ambient temperature for 15 h. The title compound was obtained as solid (247 mg, yield, 72%). $^1$H NMR (300 MHz, CD$_3$OD) δ 1.88–2.22 (m, 3H), 2.31–2.47 (m, 1H), 2.59–2.68 (m, 1H), 3.23–3.50 (m, 5H), 3.89–4.00 (m, 1H), 5.49–5.57 (m, 1H), 6.56 (dd, J=3.0, 1.0 Hz, 1H), 6.69 (s, 2H), 7.29–7.35 (m, 2H), 7.52 (dt, J=8.5, 1.0 Hz, 1H), 7.74 (dd, J=8.5, 1.7 Hz, 1H), 8.12–8.17 (m, 2H) ppm. MS (DCl/NH$_3$): m/z 321 (M+H)$^+$. Anal. Calcd. for C$_{19}$H$_{20}$N$_4$O.1.1C$_4$H$_4$O$_4$.0.4H$_2$O: C, 61.73; H, 5.58; N, 12.31. Found: C, 61.67; H, 5.52; N, 12.33.

Example 10

5-{6-[(3R)-1-azabicyclo[2.2.2]oct-3-yloxy]pyridazin-3-yl}-3-methyl-1H-indole

Example 10A 3-methyl-5-(4,4,5,5-tetramethyl-1,3,2-dioxaborolan-2-yl)-1H-indole Under N$_2$, a mixture of 5-bromo-3-methyl-1H-indole (Aldrich, 1.05 g, 5 mmol), bis(pinacolato)diboron (Aldrich, 1.40 g, 5.5 mmol), PdCl$_2$(dppf).CH$_2$Cl$_2$ (Aldrich, 122 mg, 0.15 mmol) and KOAc (Aldrich, 1.47 g, 15 mmol) in DMSO (20 mL) was stirred at 90° C. for 1 h. The reaction was monitored with TLC. After the reaction was complete, it was then diluted with EtOAc (100 mL) and washed with brine (3×10 mL). The organic solution was then concentrated and the title compound was purified by flash chromatography (SiO$_2$, Hexane:EtOAc, 80:20, R$_f$, 0.70) as solid (510 mg, yield, 40%). $^1$H NMR (300 MHz, CDCl$_3$) δ 1.38 (s, 12H), 2.35 (s, 3H), 6.98 (s, 1H), 7.34 (dd, J=8.1, 0.7, Hz, 1H), 7.65 (dd, J=8.1, 1.0 Hz, 1H), 8.12 (s, 1H) ppm. MS (DCl/NH$_3$): m/z 258 (M+H)$^+$.

Example 10B

5-{6-[(3R)-1-azabicyclo[2.2.2]oct-3-yloxy]pyridazin-3-yl}-3-methyl-1H-indole

The product of Example 10A (240 mg, 1 mmol) coupled with the product of Example 9A (250 mg, 1 mmol) according to the procedure in Example 8A, The title product was purified by preparative HPLC (Gilson, column, Symmetry® C-8 7 μm, 40×100 mm. Eluting Solvent, MeCN/H$_2$O (with 0.2% v. TFA) (v. 90/10 to 10/90 over 20 min. flow rate, 75 mL/min., uv, 250 nm) as solid (40 mg, yield, 12%). $^1$H NMR (300 MHz, CD$_3$OD) δ 1.50–1.64 (m, 1H), 1.69–1.92 (m, 2H), 2.01–2.14 (m, 1H), 2.29–2.35 (m, 1H), 2.37 (s, 3H), 2.81–3.04 (m, 5H), 3.43–3.55 (m, 1H), 5.27–5.34 (m, 1H), 7.06 (d, J=1.4 Hz, 1H), 7.24 (d, J=9.2 Hz, 1H), 7.44 (dd, J=8.5, 0.7 Hz, 1H), 7.71 (dd, J=8.8, 2.0, Hz, 1H), 8.07–8.12 (m, 2H) ppm. MS (DCl/NH$_3$): m/z 335 (M+H)$^+$.

Example 10C

5-{6-[(3R)-1-azabicyclo[2.2.2]oct-3-yloxy]pyridazin-3-yl}-3-methyl-1H-indole fumarate The product of Example 10B (40 mg, 0.12 mmol) was treated with fumaric acid (23 mg, 0.2 mmol) in EtOAc/EtOH (v. 1:1, 5 mL) at ambient temperature for 10 h. The title compound was obtained as solid (40 mg, yield, 62%). $^1$H NMR (300 MHz, CD$_3$OD) δ 1.90–2.24 (m, 3H), 2.33–2.48 (m, 4H), 2.61–2.68 (m, 1H), 3.22–3.53 (m, 5H), 3.93–4.03 (m, 1H), 5.51–5.58 (m, 1H), 6.70 (s, 3.6H), 7.08 (d, J=1.0 Hz, 1H), 7.32 (d, J=9.5 Hz, 1H), 7.45 (d, J=8.5 Hz, 1H), 7.72 (dd, J=8.8, 1.7 Hz, 1H), 8.10 (d, J=1.7 Hz, 1H), 8.17 (d, J=9.5 Hz, 1H) ppm. MS (DCl/NH$_3$): m/z 335 (M+H)$^+$. Anal. Calculated for C$_{20}$H$_{22}$N$_4$O.1.8C$_4$H$_4$O$_4$: C, 60.13; H, 5.42; N, 10.31. Found: C, 60.02; H, 5.53; N, 10.27.

Example 11

5-{2-[(3R)-1-azabicyclo[2.2.2]oct-3-yloxy]pyrimidin-5-yl}-1H-indole

Example 11A (3R)-3-[(5-bromopyrimidin-2-yl)oxy]quinuclidine

The product of Example 4A (508 mg, 4 mmol) was coupled with 5-bromo-2-iodo-pyrimidine (Aldrich, 1.42 g, 5 mmol) according to the procedure of Example 7A. The title compound was purified by chromatography (SiO$_2$, CH$_2$Cl$_2$: MeOH:NH$_3$.H$_2$O, 90:10:1, R$_f$, 0.40) as solid (760 mg, yield, 67%). $^1$H NMR (300 MHz, CD$_3$OD) δ 1.54–1.68 (m, 1H), 1.68–1.95 (m, 2H), 2.03–2.16 (m, 1H), 2.24–2.33 (m, 1H), 2.82–3.11 (m, 5H), 3.41–3.52 (m, 1H), 5.09–5.17 (m, 1H), 8.65 (s, 2H). MS (DCl/NH$_3$): 284 (M+H)$^+$ 286 (M+H)$^+$.

Example 11B

5-{2-[(3R)-1-azabicyclo[2.2.2]oct-3-yloxy]pyrimidin-5-yl}-1H-indole

The product of Example 11A (283 mg, 1 mmol) was coupled with 5-indolylboronic acid (Aldrich, 193 mg, 1.2 mmol) according to the procedure of Example 3A. The title product was purified by preparative HPLC (Gilson, column, Symmetry® C-8 7 μm, 40×100 mm. Eluting Solvent, MeCN/H$_2$O (with 0.2% v. TFA) (v. 90/10 to 10/90 over 20 min. flow rate, 75 mL/min., uv, 250 nm) as solid (40 mg, yield, 12%). $^1$H NMR (300 MHz, CD$_3$OD) δ 1.50–1.63 (m, 1H), 1.67–1.93 (m, 2H), 2.04–2.17 (m, 1H), 2.24–2.31 (m, 1H), 2.75–3.05 (m, 5H), 3.38–3.48 (m, 1H), 5.14–5.21 (m, 1H), 6.53 (dd, J=3.1, 0.7 Hz, 1H), 7.30 (d, J=3.1 Hz, 1H), 7.35 (dd, J=8.5, 1.7 Hz, 1H), 7.51 (dt, J=8.5, 0.7 Hz, 1H), 7.80 (dd, J=1.7, 0.7 Hz, 1H), 8.82 (s, 2H) ppm. MS (DCl/NH$_3$): m/z 321 (M+H)$^+$.

Example 11C

5-{2-[(3R)-1-azabicyclo[2.2.2]oct-3-yloxy]pyrimidin-5-yl}-1H-indole hemifumarate The product of 11B (40 mg, 0.12 mmol) was treated with fumaric acid (12 mg, 0.1 mmol) in EtOAc/EtOH (v. 1:1, 3 mL) at ambient temperature for 10 h. The title compound was obtained as solid (42 mg, yield, 88%). $^1$H NMR (300 MHz, CD$_3$OD) δ 1.72–2.10 (m, 3H), 2.20–2.34 (m, 1H), 2.43–2.51 (m, 1H), 3.04–3.43 (m, 5H), 3.65–3.76 (m, 1H), 5.28–5.36 (m, 1H), 6.52 (dd, J=3.1, 1.1 Hz, 1H), 6.67 (s, 1H), 7.30 (d, J=3.1 Hz, 1H), 7.35 (dd, J=8.5, 1.7 hz, 1H), 7.51 (dt, J=8.5, 0.7 Hz, 1H), 7.80 )dd, J=1.7, 0.7 Hz, 1H), 8.84 (s, 2H) ppm. MS (DCl/NH$_3$): m/z 321 (M+H)$^+$. Anal. Calcd. for C$_{19}$H$_{20}$N$_4$O.0.6C$_4$H$_4$O$_4$: C, 65.90; H, 5.79; N, 14.36. Found: C, 65.65; H, 5.24; N, 14.41.

Example 12

4-{2-[(3R)-1-azabicyclo[2.2.2]oct-3-yloxy]pyrimidin-5-yl}-1H-indole

Example 12A

4-{2-[(3R)-1-azabicyclo[2.2.2]oct-3-yloxy]pyrimidin-5-yl}-1H-indole

The product of Example 11A (170 mg, 0.6 mmol) was coupled with 4-(4,4,5,5-tetra-methyl-[1,3,2]dioxaborolan-2-yl)-1H-indole ((ref. WO02055517, 146 mg, 0.6 mmol) according to the procedure in Example 8A. The title compound was purified by chromatography (SiO$_2$, CH$_2$Cl$_2$: MeOH:NH$_3$.H$_2$O, 90:10:1, R$_f$, 0.10) as a solid (76 mg, yield, 40%). $^1$H NMR (300 MHz, CD$_3$OD) δ 1.50–1.64 (m, 1H), 1.67–1.93 (m, 2H), 2.05–2.19 (m, 1H), 2.25–2.33 (m, 1H), 2.73–3.12 (m, 5H), 3.39–3.50 (m, 1H), 5.17–5.25 (m, 1H), 6.55 (dd, J=3.4, 1.0 Hz, 1H), 7.11 (dd, J=7.1, 1.0, Hz, 1H), 7.23 (t, J=8.1 Hz, 1H), 7.35 (d, J=3.1 Hz, 1H), 7.44–7.49 (m, 1H), 8.85 (s, 2H) ppm. MS (DCl/NH$_3$): m/z 321 (M+H)$^+$.

Example 12B

4-{2-[(3R)-1-azabicyclo[2.2.2]oct-3-yloxy]pyrimidin-5-yl}-1H-indole fumarate

The product of Example 12A (76 mg, 0.24 mmol) was treated with fumaric acid (29 mg, 0.25 mmol) in EtOAc/EtOH (v. 1:1, 4 mL) at ambient temperature for 10 hours. The title compound was obtained as solid (94.6 mg, yield, 90%). $^1$H NMR (300 MHz, CD$_3$OD) δ 1.88–2.21 (m, 3H), 2.33–2.48 (m, 1H), 2.59–2.66 (m, 1H), 3.22–3.50 (m, 5H), 3.84–3.95 (m, 1H), 5.41–5.49 (m, 1H), 6.55 (dd, J=3.4, 1.0 Hz, 1H), 6.68 (s, 2H), 7.11 (dd, J=7.5, 1.0 Hz, 1H), 7.24 (t, J=8.1 Hz, 1H), 7.36 (d, J=3.1 Hz, 1H), 7.48 (dt, J=8.1, 0.7 Hz, 1H), 8.89 (s, 2H) ppm. MS (DCl/NH$_3$): m/z 321 (M+H)$^+$. Anal. Calculated for C$_{19}$H$_{20}$N$_4$O.C$_4$H$_4$O$_4$: C, 63.29; H, 5.54; N, 12.84. Found: C, 62.95; H, 5.85; N, 12.61.

Example 13

5-{2-[(3S)-1-azabicyclo[2.2.2]oct-3-yloxy]pyrimidin-5-yl}-1H-indole

Example 13A (3R)-1-azabicyclo[2.2.2]oct-3-yl benzoate (L)-tartrate (+/−)-3-Quinuclidinol benzoate (Sigma, 17.9 g, 77.5 mmol) was treated with L-tartaric acid (Aldrich, 99% ee, 11.63 g, 77.5 mmol) in EtOH (80%, 222 mL) at ambient temperature for 1 week. The white solid was filtered off and dried under reduced pressure. 6.5 g of 3-(R)-quinuclidinol benzoate.(L)-tartrate was obtained with ~80% ee (assayed by HPLC. HPLC conditions: chiralpak AD column 25 cm×4 mm ID. solvent, EtOH:hexanes=15:85. flow rate, 1 mL/min. uv, 220 nm. Retention time: (S)-3-quinuclidinol benzoate, 7.87 min; (R)-3-quinuclidinol benzoate 13.3 min.) Recrystallization of the above solid in EtOH (80%, 35 mL) gave the title product (4.5 g, yield, 15%, >98% ee). MS (DCl/NH$_3$) m/z 232 (M+H)$^+$.

Example 13B (3R)-quinuclidin-3-ol

The product of the Example 13A (4.5 g, 11.8 mmol) was treated with Hydrolysis was NaOH (15%, 40 mL) MeOH (40 mL) at 50° C. for 10 h. The methanol was removed under reduced pressure and the residue was extracted with chloroform (4×80 mL). The extracts were combined and dried over MgSO$_4$ (anhydrous). The drying agents were filtered off and the filtrate was concentrated to give the title product as white solid (1.35 g, yield, 0.90%). MS (DCl/NH$_3$) m/z 128 (M+H)$^+$.

Example 13C (3S)-1-azabicyclo[2.2.2]oct-3-yl benzoate (D)-tartrate

The mother liquid of Example 13A was combined and concentrated under reduced pressure. The residue was then treated with NaOH (1 N, 50 mL) at room temperature for 30 min. It was extracted with chloroform (3×mL) The extracts were combined and dried (MgSO$_4$). The drying agents were filtered off. The filtrates was concentrated to give 3-quinuclidinol benzoate (15.25 g, 66 mmol) It was then treated with (D)-tartaric acid (Aldrich, 97% ee, 9.9 g, 66 mmol,) in EtOH (80%, 190 ml) at room temperature for 3 days according to the procedure of Example 1A. The title product was obtained (7.0 g, yield, 28%, 92.3% ee).

Example 13D (3S)-quinuclidin-3-ol

The product of Example 13C (7.0 g, 18.4 mmol) was treated with NaOH (aqueous) according to the procedure of Example 1B. The title product was obtained as white solid (2.0 g, yield, 86%) MS (DCl/NH$_3$) m/z 128 (M+H)$^+$.

Example 13E (3S)-3-[(5-bromopyrimidin-2-yl)oxy]quinuclidine

The product of Example 13 (508 mg, 4 mmol) was coupled with 2-iodo-5-bromo-pyrimidine (1.42 g, 5 mmol) according to the procedure of Example 7A. The title compound was purified by chromatography (SiO$_2$, CH$_2$Cl$_2$: MeOH:NH$_3$.H$_2$O, 90:10:1, R$_f$, 0.20) as solid (780 mg, yields, 69%) as a solid. $^1$H NMR (300 MHz, CD$_3$OD) δ 1.47–1.61 (m, 1H), 1.63–1.90 (m, 2H), 1.96–2.12 (m, 1H), 2.19–2.27 (m, 1H), 2.73–3.03 (m, 5H), 3.33–3.45 (m, 1H), 5.05–5.14 (m, 1H), 8.64 (s, 2H) ppm. MS (DCl/NH$_3$): 284 (M+H)$^+$ 286 (M+H)$^+$.

Example 13F

5-{2-[(3S)-1-azabicyclo[2.2.2]oct-3-yloxy]pyrimidin-5-yl}-1H-indole

The product of Example 13E (283 mg, 1 mmol) was coupled with 5-indolylboronic acid (193 mg, 1.2 mmol) according to the procedure of Example 3A, The title product was purified by preparative HPLC (Gilson, column, Symmetry® C-8 7 μm, 40×100 mm. Eluting Solvent, MeCN/ H$_2$O (with 0.2% v. TFA) (v. 90/10 to 10/90 over 20 min.) Flow rate, 75 mL/min., uv, 250 nm) as solid (120 mg, yield, 38%). $^1$H NMR (300 MHz, CD$_3$OD) δ 1.50–1.63 (m, 1H), 1.66–1.92 (m, 2H), 2.03–2.18 (m, 1H), 2.24–2.32 (m, 1H), 2.75–3.07 (m, 5H), 3.38–3.49 (m, 1H), 5.13–5.21 (m, 1H), 6.53 (dd, J=3.0, 0.7 Hz, 1H), 7.30 (d, J=3.4 Hz, 1H), 7.35 (dd, J=8.5, 1.7 Hz, 1H), 7.51 (dt, J=9.2, 0.7 Hz, 1H), 7.80 (dd, J=1.7, 0.7 Hz, 1H), 8.81 (s, 2H) ppm. MS (DCl/NH$_3$): m/z 321 (M+H)$^+$.

Example 13G

5-{2-[(3S)-1-azabicyclo[2.2.2]oct-3-yloxy]pyrimidin-5-yl}-1H-indole hemifumarate The product of Example 13F (120 mg, 0.38 mmol) was treated with fumaric acid (44 mg, 0.38 mmol) in EtOAc/ EtOH (v. 1:1, 10 mL). The title compound was obtained as solid (123 mg, yield, 84%). $^1$H NMR (300 MHz, CD$_3$OD) δ 1.75–2.13 (m, 3H), 2.22–2.37 (m, 1H), 2.46–2.54 (m, 1H), 3.03–3.45 (m, 5H), 3.68–3.79 (m, 1H), 5.30–5.38 (m, 1H), 6.52 (dd, J=3.1, 1.1 Hz, 1H), 6.67 (s, 1.2H), 7.30 (d, J=3.1 Hz, 1H), 7.35 (dd, J=8.5, 1.7 Hz, 1H), 7.51 (dt, J=8.5, 0.7 Hz, 1H), 7.80 (dd, J=1.7, 0.7 Hz, 1H), 8.82 (s, 2H) ppm. MS (DCl/NH$_3$): m/z 321 (M+H)$^+$. Anal. Calculated for C$_{19}$H$_{20}$N$_4$O.0.6C$_4$H$_4$O$_4$: C, 65.90; H, 5.79; N, 14.36. Found: C, 65.62; H, 5.76; N, 14.40.

Example 14

5-[4-(1-azabicyclo[2.2.2]oct-3-yloxy)phenyl]-3-methyl-1H-indazole trifluoroacetate The product of Example 1A (200 mg, 0.61 mmol) was coupled with t-Butyl-(3-Methyl-5-trimethylstannanyl-indazole)-1-carboxylate (ref. U.S. 2003199511, 294 mg, 1 mmol) according to the procedure of Example 2B. The title product was purified by preparative HPLC (Gilson, column, Symmetry® C-8 7 μm, 40×100 mm. Eluting Solvent, MeCN/H$_2$O (with 0.2% v. TFA) (v. 90/10 to 10/90 over 20 min. flow rate, 75 mL/min., uv, 250 nm) as solid (70 mg, yield, 26%). $^1$H NMR (300 MHz, CD$_3$OD) δ 1.85–2.13 (m, 3H), 2.22–2.37 (m, 1H), 2.46–2.50 (m, 1H), 2.58 (s, 3H), 3.23–3.45 (m, 5H), 3.78–3.86 (m, 1H), 4.90–5.00 (m, 1H), 7.07 (dt, J=8.8, 2.0 Hz, 2H), 7.50 (d, J=8.8 Hz, 1H), 7.61–7.68 (m, 3H), 7.85 (s, 1H) ppm. MS (DCl/NH$_3$): m/z 334 (M+H)$^+$. Anal. Calculated for C$_{21}$H$_{23}$N$_3$O.1.0CF$_3$CO$_2$H.0.5H$_2$O: C, 60.52; H, 5.52; N, 9.21. Found: C, 60.79; H, 5.39; N, 9.17.

Example 15

6-[4-(1-azabicyclo[2.2.2]oct-3-yloxy)phenyl]-1,3-benzothiazol-2-amine

Example 15A

3-[(4'-nitro-1,1'-biphenyl-4-yl)oxy]quinuclidine

3-Quinuclidinol (Aldrich, 0.51 g, 4 mmol) coupled with 4'-nitro-1,1'-biphenyl-4-ol (TCI, 0.43 g, 2 mmol) with DIAD (di-isopropyl azadicarboxylate, Aldrich, 0.81 g, 4 mmol) and Ph$_3$P (Aldrich, 1.04 g, 4 mmol) in THF (anhydrous, Aldrich, 40 mL) at ambient temperature for two days. The reaction mixture was concentrated. The title product was purified by chromatography (SiO$_2$, CH$_2$Cl$_2$:MeOH:NH$_3$.H$_2$O, 90:10:1, R$_f$, 0.20) as solid (400 mg, yield, 62%). $^1$H NMR (300 MHz, CD$_3$OD) δ 1.45–1.57 (m, 1H), 1.63–1.91 (m, 2H), 1.97–2.12 (m, 1H), 2.17–2.24 (m, 1H), 2.66–3.00 (m, 5H), 3.30–3.41 (m, 1H), 4.56–4.64 (m, 1H), 7.05 (dt, J=8.8, 2.6 Hz, 2H), 7.68 (dt, J=9.2, 2.6 Hz, 2H), 7.82 (dt, J=8.8, 2.7 Hz, 2H), 8.28 (dt, J=8.8, 2.8 Hz, 2H) ppm. MS (DCl/NH$_3$) m/z 325 (M+H)$^+$.

Example 15B

4'-(1-azabicyclo[2.2.2]oct-3-yloxy)-1,1'-biphenyl-4-amine

The product of Example 15A (300 mg, 0.92 mmol) was treated with Pd/C (Aldrich, wt. 10%, 30 mg) in methanol (20 mL) under H$_2$ at ambient temperature for 30 min. After the reaction was complete, the catalyst was removed through a short column of diatomaceous earth. The filtrate was concentrated under reduced pressure to provide the title compound (200 mg, yield, 74%). $^1$H NMR (300 MHz, CD$_3$OD) δ 1.44–1.58 (m, 1H), 1.63–1.89 (m, 2H), 1.99–2.13 (m, 1H), 2.15–2.23 (m, 1H), 2.72–3.04 (m, 5H), 3.29–3.39 (m, 1H), 4.50–4.58 (m, 1H), 6.77 (dt, J=8.8, 2.5 Hz, 2H), 6.91 (dt, J=8.8, 2.4 Hz, 2H), 7.32 (dt, J=8.5, 2.5 Hz, 2H), 7.43 (dt, J=9.2, 2.8 Hz, 2H) ppm. MS (DCl/NH$_3$) m/z 295 (M+H)$^+$.

Example 15C

6-[4-(1-azabicyclo[2.2.2]oct-3-yloxy)phenyl]-1,3-benzothiazol-2-amine

The product of Example 15B (200 mg, 0.68 mmol) and KSCN (Aldrich, 140 mg, 1.52 mmol) were dissolved in HOAc (5 mL). Bromine [Aldrich, 99%, 40 μL, 0.76 mmol, in HOAc (1 mL) was added slowly to the above solution over 5 min. The mixture was stirred at ambient temperature for additional 1 h. and then quenched with aqueous NaOH (10%, 20 mL) at 5–10° C. It was then extracted with CHCl$_3$/$^i$PrOH (v. 10:1, 2×50 mL). The extracts were combined and concentrated under reduced pressure. The title compound was purified by chromatography (SiO$_2$, CH$_2$Cl$_2$: MeOH:NH$_3$.H$_2$O, 90:10:1, R$_f$, 0.10) as solid (140 mg, yield, 59%). $^1$H NMR (300 MHz, CD$_3$OD) δ 1.27–1.37 (m, 1H), 1.51–1.72 (m, 2H), 1.79–1.88 (m, 1H), 2.02–2.07 (m, 1H), 2.51–2.84 (m, 5H), 3.21–3.39 (m, 1H), 4.45–4.52 (m, 1H), 6.97 (d, J=8.8 Hz, 2H), 7.35 (d, J=8.5 Hz, 7.45 (dd, J=8.5, 2.1 Hz, 1H), 7.55 (d, J=8.5, 2H), 7.90 (d, J=2.0 Hz, 1H) ppm. MS (DCl/NH$_3$) m/z 352 (M+H)$^+$.

Example 15D

6-[4-(1-azabicyclo[2.2.2]oct-3-yloxy)phenyl]-1,3-benzothiazol-2-amine bistrifluoroacetate The product of Example 15C (140 mg, 0.4 mmol) was treated with trifluroacetic acid (Aldrich, 99%, 114 mg, 80 μL, 1 mmol) in $^i$PrOH (5 mL) at ambient temperature for 15 h. The title compound was obtained as solid (90 mg, yield, 39%). $^1$H NMR (300 MHz, DMSO-D$_6$) δ 1.75–2.16 (m, 3H), 2.30–2.52 (m, 2H), 3.03–3.45 (m, 5H), 3.75–3.82 (m, 1H), 4.78–4.85 (m, 1H), 7.05 (d, J=8.8 Hz, 2H), 7.38 (d, J=8.5 Hz, 1H), 7.50 (dd, J=8.5, 2.1 Hz, 1H), 7.62 (d, J=8.8 Hz, 2H), 7.76 [s(broad.), 2H], 7.96 (d, J=1.7 Hz, 1H) ppm. MS (DCl/NH$_3$): m/z 352 (M+H)$^+$. Anal. Calculated for C$_{20}$H$_{21}$N$_3$OS.2.08CF$_3$CO$_2$H C, 49.30; H, 3.95; N, 7.14. Found: C, 49.70; H, 3.42; N, 7.03.

Example 16

N-[4-(3-methyl-1H-indazol-5-yl)phenyl]quinuclidin-3-amine

Example 16A

N-(4-iodophenyl)quinuclidin-3-amine

3-Quinuclidinone hydrochloride (Aldrich, 3.22 g, 20 mmol) was treated with 4-iodo-aniline (Aldrich, 2.19 g, 10 mmol), Na$_2$SO$_4$ (anhydrous, Aldrich, 7.40 g, 50 mmol) and NaBH(OAc)$_3$ (Aldrich, 3.16 g, 15 mmol) in HOAc (25 mL) at ambient temperature for 15 h. After the reaction was complete, the reaction mixture was slowly poured into a flask containing 75 mL of saturated NaHCO$_3$ and stirred for 20 min. It was then extracted with EtOAc (3×100 mL). The extracts were combined and washed with brine (2×20 mL). The organic solution was concentrated under reduced pressure and the title compound was purified by chromatography (SiO$_2$, CH$_2$Cl$_2$:MeOH:NH$_3$.H$_2$O, 90:10:2, R$_f$ 0.10) as oil (3.24 g, yield, 98%). $^1$H NMR (300 MHz, CD$_3$OD,) δ 1.70–1.81 (m, 1H), 1.93–2.04 (m, 2H), 2.08–2.24 (m, 2H), 2.89 (ddd, J=12.9, 5.1, 2.7 Hz, 1H), 3.12–3.28 (m, 4H), 3.64 (ddd, J=12.9, 9.5, 2.4 Hz, 1H), 3.79–3.85 (m, 1H), 6.46 (dt, J=9.0, 2.7 Hz, 2H), 7.39 (dt, J=9.1, 2.7 Hz, 2H) ppm. MS (DCl/NH$_3$) m/z 329 (M+H)$^+$.

Example 16B

N-[4-(3-methyl-1H-indazol-5-yl)phenyl]quinuclidin-3-amine trifluoroacetate

The product of Example 16A (200 mg, 0.61 mmol) was coupled with t-Butyl-(3-Methyl-5-trimethylstannanyl-indazole)-1-carboxylate (ref. U.S. 2003199511, 294 mg, 1 mmol) according to the procedure of Example 2B. The title product was purified by preparative HPLC (Gilson, column, Symmetry® C-8 7 μm, 40×100 mm. Eluting Solvent, MeCN/H$_2$O (with 0.2% v. TFA) (v. 90/10 to 10/90 over 20 min.) Flow rate, 75 mL/min., uv, 250 nm) as solid (28 mg, yield, 10%). $^1$H NMR (300 MHz, CD$_3$OD) δ 1.85–1.96 (m, 1H), 2.08–2.15 (m, 2H), 2.24–2.40 (m, 2H), 2.59 (s, 3H), 3.02–3.15 (m, 1H), 3.20–3.45 (m, 4H), 3.78–3.88 (m, 1H), 3.98–4.06 (m, 1H), 6.77 (dt, J=8.8, 2.0 Hz, 2H), 7.46–7.52 (m, 3H), 7.59 (dd, J=8.9, 1.6 Hz, 1H), 7.78 (s, 1H) ppm. MS (DCl/NH$_3$): m/z 333 (M+H)$^+$. Anal. Calculated for C$_{21}$H$_{24}$N$_4$.1.25CF$_3$CO$_2$H: C, 59.43; H, 5.36; N, 11.80. Found: C, 59.20; H, 4.96; N, 11.62.

Example 17

Determination of Biological Activity

To determine the effectiveness of representative compounds of this invention as α7 nAChRs, the compounds of the invention were evaluated according to the [3H]-methyllycaconitine (MLA) binding assay and considering the [3H]-cytisine binding assay, which were performed as described below.

[3H]-Cytisine Binding

Binding conditions were modified from the procedures described in Pabreza L A, Dhawan, S, Kellar K J, [$^3$H]-Cytisine Binding to Nicotinic Cholinergic Receptors in Brain, Mol. Pharm. 39: 9–12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100–200 μg of protein and 0.75 nM [3H]-cytisine (30 C$_i$/mmol; Perkin Elmer/NEN Life Science Products, Boston, Mass.) were incubated in a final volume of 500 μL for 75 minutes at 4° C. Seven log-dilution concentrations of each compound were tested in duplicate. Non-specific binding was determined in the presence of 10 μM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard MicroScint-20® scintillation cocktail (40 μL) was added to each well and radioactivity determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/1+[Ligand]/K$_D$].

[3H]-Methyllycaconitine (MLA) Binding

Binding conditions were similar to those for [3H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM CaCl$_2$, 2 mM MgCl$_2$, and 50 mM Tris-Cl, pH 7.4, 22° C.). Samples containing 100–200 μg of protein, 5 nM [3H]-MLA (25 C$_i$/mmol; Perkin Elmer/NEN Life Science Products, Boston, Mass.) and 0.1% bovine serum albumin (BSA, Millipore, Bedford, Mass.) were incubated in a final volume of 500 μL for 60 minutes at 22° C. Seven log-dilution concentrations of each compound were tested in duplicate. Non-specific binding was determined in the presence of 10 μM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20® scintillation cocktail (40 μL) was added to each well and radioactivity was determined using a Packard TopCount® instrument. The IC$_{50}$ values were determined by nonlinear regression in Microsoft Excel® software. $K_i$ values were calculated from the $IC_{50}$s using the Cheng-Prusoff equation, where $K_i=IC_{50}/1+$[Ligand]/$K_D$].

Compounds of the invention had $K_i$ values of from about 1 nanomolar to about 10 micromolar when tested by the MLA assay, many having a $K_i$ of less than 1 micromolar. [3H]-Cytisine binding values of compounds of the invention ranged from about 50 nanomolar to at least 100 micromolar. The determination of preferred compounds typically considered the $K_i$ value as measured by MLA assay in view of the $K_i$ value as measured by [3H]-cytisine binding, such that in the formula D=$K_{i\ 3H\text{-}cytisine}/K_{i\ MLA}$, D is about 50. Preferred compounds typically exhibited greater potency at α7 receptors compared to α4β2 receptors.

Compounds of the invention are α7 nAChRs ligands that modulate function of α7 nAChRs by altering the activity of the receptor. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula (I):

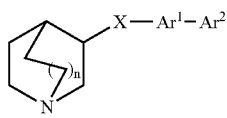
(I)

or a pharmaceutically acceptable salt, ester, amide, or prodrug thereof, wherein:

n is 0, 1, or 2;

X is selected from the group consisting of O, S, and $NR^1$;

$Ar^1$ is a 6-membered aromatic ring containing 0, 1, 2, 3, or 4 nitrogen atoms;

$Ar^2$ is a group of the formula:

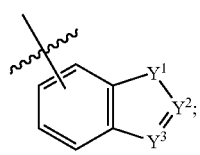
(a)

$Y^1$ is independently selected from O, S, $N(R^2)$, and $C(R^3)$;

$Y^2$ and $Y^3$ are each independently selected from the group consisting of N and $C(R^3)$;

$R^1$ and $R^2$ at each occurrence are each independently selected from the group consisting of hydrogen and alkyl;

$R^3$ at each occurrence is independently selected from the group consisting of hydrogen, halogen, alkyl, aryl, —$OR^4$, and —$NR^5R^6$;

$R^4$ is selected from the group consisting of hydrogen, alkyl, aryl, alkylcarbonyl, and arylcarbonyl; and $R^5$ and $R^6$ at each occurrence are each independently selected from the group consisting of hydrogen, alkyl, aryl, alkylcarbonyl, alkoxycarbonyl, aryloxycarbonyl, and arylcarbonyl, provided that one of $R^5$ and $R^6$ is hydrogen or alkyl.

2. The compound of claim 1, wherein $Ar^1$ is a group of the formula:

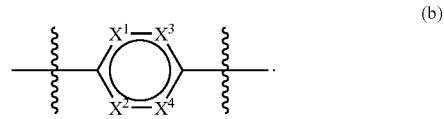
(b)

wherein:

$X^1$, $X^2$, $X^3$, and $X^4$ are each independently selected from the group consisting of N and —$CR^{10}$; and $R^{10}$ at each occurrence is independently selected from the group consisting of hydrogen and alkyl.

3. The compound of claim 1, wherein $Ar^1$ is selected from the group consisting of:

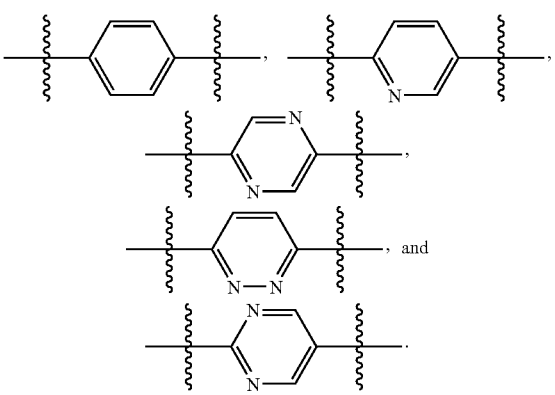

4. The compound of claim 1, wherein $Ar^2$ is selected from the group consisting of:

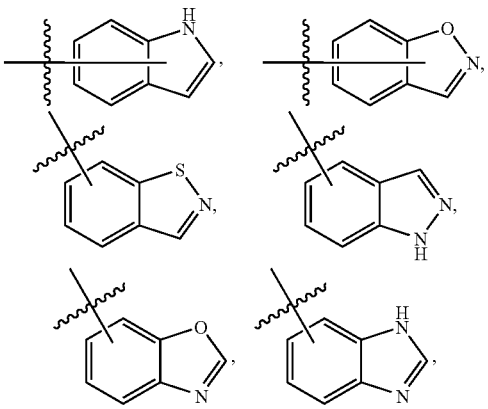

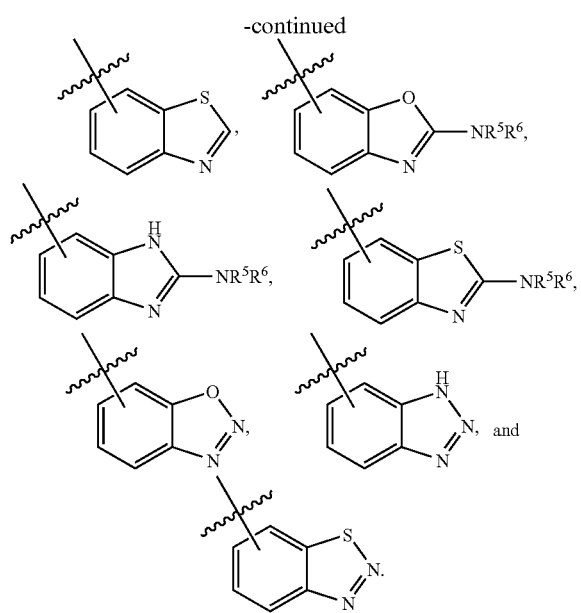

5. The compound of claim 1, or a pharmaceutically acceptable salt, ester, amide, or prodrug thereof, selected from the group consisting of:
   3-[4-(1-azabicyclo[2.2.2]oct-3-yloxy)phenyl]-1H-indole;
   4-[4-(1-azabicyclo[2.2.2]oct-3-yloxy)phenyl]-1H-indole;
   5-[4-(1-azabicyclo[2.2.2]oct-3-yloxy)phenyl]-1H-indole;
   5-{4-[(3R)-1-azabicyclo[2.2.2]oct-3-yloxy]phenyl}-1H-indole;
   6-[4-(1-azabicyclo[2.2.2]oct-3-yloxy)phenyl]-1H-indole;
   2-[4-(1-azabicyclo[2.2.2]oct-3-yloxy)phenyl]-1H-indole;
   5-[6-(1-azabicyclo[2.2.2]oct-3-yloxy)pyridazin-3-yl]-1H-indole;
   4-[6-(1-azabicyclo[2.2.2]oct-3-yloxy)pyridazin-3-yl]-1H-indole;
   5-{6-[(3R)-1-azabicyclo[2.2.2]oct-3-yloxy]pyridazin-3-yl}-1H-indole;
   5-{6-[(3R)-1-azabicyclo[2.2.2]oct-3-yloxy]pyridazin-3-yl}-3-methyl-1H-indole;
   5-{2-[(3R)-1-azabicyclo[2.2.2]oct-3-yloxy]pyrimidin-5-yl}-1H-indole;
   4-{2-[(3R)-1-azabicyclo[2.2.2]oct-3-yloxy]pyrimidin-5-yl}-1H-indole;
   5-{2-[(3S)-1-azabicyclo[2.2.2]oct-3-yloxy]pyrimidin-5-yl}-1H-indole;
   5-[4-(1-azabicyclo[2.2.2]oct-3-yloxy)phenyl]-3-methyl-1H-indazole;
   (6-[4-(1-azabicyclo[2.2.2]oct-3-yloxy)phenyl]-1,3-benzothiazol-2-amine; and
   N-[4-(3-methyl-1H-indazol-5-yl)phenyl]quinuclidin-3-amine.

6. A pharmaceutical composition comprising a therapeutically effective amount of a compound of claim 1 in combination with a pharmaceutically acceptable carrier.

7. The compound of claim 1, or a pharmaceutically acceptable salt, ester, amide, or prodrug thereof, wherein the compound is 5-{6-[(3R)-1-azabicyclo[2.2.2]oct-3-yloxy]pyridazin-3-yl}-1H-indole.

* * * * *

UNITED STATES PATENT AND TRADEMARK OFFICE
CERTIFICATE OF CORRECTION

PATENT NO. : 7,160,876 B2  Page 1 of 1
APPLICATION NO. : 10/744208
DATED : January 9, 2007
INVENTOR(S) : Ji Jianguo et al.

It is certified that error appears in the above-identified patent and that said Letters Patent is hereby corrected as shown below:

Col. 56, line 30 replace "The compound of claim 1, or a pharmaceutically acceptable salt, ester, amide or prodrug thereof, wherein the compound is 5-{6-[(3R)-1-azabicyclo[2.2.2]oct-3-yloxy]pyridazin-3-yl}-1H-indole."

with -- A compound that is 5-{6-[(3R)-1-azabicyclo[2.2.2]oct-3-yloxy]pyridazin-3-yl}-1H-indole or a pharmaceutically acceptable salt thereof. --

Signed and Sealed this

Twenty Second Day of April, 2008

JON W. DUDAS
*Director of the United States Patent and Trademark Office*